US012799115B2

(12) United States Patent
Mahadevan

(10) Patent No.: US 12,799,115 B2
(45) **Date of Patent: *Nov. 17, 2026**

(54) PHOTOSTABLE MIMICS OF MACULAR PIGMENT

(71) Applicant: Johnson & Johnson Vision Care, Inc., Jacksonville, FL (US)

(72) Inventor: Shivkumar Mahadevan, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1215 days.

This patent is subject to a terminal disclaimer.

(21) Appl. No.: 17/456,659

(22) Filed: Nov. 29, 2021

(65) Prior Publication Data

US 2022/0194944 A1 Jun. 23, 2022

Related U.S. Application Data

(60) Provisional application No. 63/127,382, filed on Dec. 18, 2020.

(51) Int. Cl.

| | |
|---|---|
| ***C07D 487/00*** | (2006.01) |
| ***C07D 219/06*** | (2006.01) |
| ***C08K 5/34*** | (2006.01) |
| ***C08K 5/3437*** | (2006.01) |
| ***C09B 15/00*** | (2006.01) |
| ***C09B 23/01*** | (2006.01) |
| ***G02B 1/04*** | (2006.01) |
| ***G02B 5/00*** | (2006.01) |
| ***G02C 7/04*** | (2006.01) |
| ***G02C 7/10*** | (2006.01) |

(52) U.S. Cl.

CPC ......... *C07D 487/00* (2013.01); *C07D 219/06* (2013.01); *C08K 5/34* (2013.01); *C08K 5/3437* (2013.01); *C09B 15/00* (2013.01); *C09B 23/005* (2013.01); *C09B 23/0058* (2013.01); *G02B 1/043* (2013.01); *G02B 5/003* (2013.01); *G02C 7/04* (2013.01); *G02C 7/10* (2013.01); *G02C 7/108* (2013.01)

(58) Field of Classification Search

CPC .. C07D 487/00; C07D 219/06; C08K 5/3437; C08K 5/34; C09B 15/00; C09B 23/005; C09B 23/0058; G02B 1/043; G02B 5/003; G02C 7/04; G02C 7/10; G02C 7/108

See application file for complete search history.

(56) References Cited

U.S. PATENT DOCUMENTS

| | | | |
|---|---|---|---|
| 3,196,150 | A | 7/1965 | Martin |
| 3,376,303 | A | 4/1968 | Fuchs et al. |
| 3,408,429 | A | 10/1968 | Wichterle |
| 3,660,545 | A | 5/1972 | Wichterle |
| 3,769,294 | A | 10/1973 | Catino et al. |
| 3,808,178 | A | 4/1974 | Gaylord |
| 4,113,224 | A | 9/1978 | Clark et al. |
| 4,120,570 | A | 10/1978 | Gaylord |
| 4,136,250 | A | 1/1979 | Mueller et al. |
| 4,153,641 | A | 5/1979 | Deichert et al. |
| 4,197,266 | A | 4/1980 | Clark et al. |
| 4,436,887 | A | 3/1984 | Chromecek et al. |
| 4,495,313 | A | 1/1985 | Larsen |
| 4,659,763 | A | 4/1987 | Gallucci et al. |
| 4,659,782 | A | 4/1987 | Spinelli |
| 4,659,783 | A | 4/1987 | Spinelli |
| 4,716,234 | A | 12/1987 | Dunks et al. |
| 4,740,533 | A | 4/1988 | Su et al. |
| 4,889,664 | A | 12/1989 | Kindt-Larsen et al. |
| 4,910,277 | A | 3/1990 | Bambury et al. |
| 4,997,897 | A | 3/1991 | Melpolder |
| 5,006,622 | A | 4/1991 | Kunzler et al. |
| 5,034,461 | A | 7/1991 | Lai et al. |
| 5,039,459 | A | 8/1991 | Kindt-Larsen et al. |
| 5,070,215 | A | 12/1991 | Bambury et al. |
| 5,236,969 | A | 8/1993 | Kunzler et al. |
| 5,244,981 | A | 9/1993 | Seidner et al. |
| 5,270,418 | A | 12/1993 | Kunzier et al. |
| 5,298,533 | A | 3/1994 | Nandu et al. |
| 5,314,960 | A | 5/1994 | Spinelli et al. |
| 5,331,067 | A | 7/1994 | Seidner et al. |
| 5,371,147 | A | 12/1994 | Spinelli et al. |
| 5,470,932 | A | 11/1995 | Jinkerson |
| 5,480,927 | A | 1/1996 | Janssen et al. |
| 5,729,322 | A | 3/1998 | Collins et al. |
| 5,760,100 | A | 6/1998 | Nicolson et al. |
| 5,776,999 | A | 7/1998 | Nicolson et al. |
| 5,789,461 | A | 8/1998 | Nicolson et al. |
| 5,824,719 | A | 10/1998 | Kunzler et al. |
| 5,849,811 | A | 12/1998 | Nicolson et al. |
| 5,872,118 | A | 2/1999 | Kelley et al. |
| 5,916,719 | A | 6/1999 | Kim et al. |
| 5,944,853 | A | 8/1999 | Molock et al. |

(Continued)

FOREIGN PATENT DOCUMENTS

| | | | |
|---|---|---|---|
| CN | 203965745 | U | 11/2014 |
| CN | 106349212 | A | 1/2017 |

(Continued)

OTHER PUBLICATIONS

PCT International Preliminary Report on Patentability, dated Mar. 1, 2022, for PCT Int'l Appln. No. PCT/IB2020/057732.

(Continued)

*Primary Examiner* — Patrick D Niland
(74) *Attorney, Agent, or Firm* — Raef M. Shaltout

(57) ABSTRACT

Described are visible light absorbing compounds. The compounds have a visible light absorption maximum between 430 and 480 nm and a full width half maximum (FWHM) at the visible light absorption maximum of at least 35 nm and up to 150 nanometers, wherein the compounds are photostable. The compounds are also thermally stable. The compounds substantially mimic the visible light absorbance properties of macular pigment while remaining photostable and thermally stable. The compounds may be used in a variety of articles, including ophthalmic devices.

6 Claims, 3 Drawing Sheets

(56) References Cited

U.S. PATENT DOCUMENTS 5,945,465 A 8/1999 Ozark et al.
5,962,548 A 10/1999 Vanderlaan et al.
5,965,631 A 10/1999 Nicolson et al.
5,977,219 A 11/1999 Ravichandran et al.
5,998,498 A 12/1999 Vanderlaan et al.
6,020,445 A 2/2000 Vanderlaan et al.
6,022,158 A 2/2000 Nakayama et al.
6,087,415 A 7/2000 Vanderlaan et al.
6,158,862 A 12/2000 Patel et al.
6,166,218 A 12/2000 Ravichandran et al.
6,207,244 B1 3/2001 Hesch
6,244,707 B1 6/2001 Faubl
6,367,929 B1 4/2002 Maiden et al.
6,373,615 B1 4/2002 Mann et al.
6,420,453 B1 7/2002 Bowers et al.
6,423,761 B1 7/2002 Bowers et al.
6,527,977 B2 3/2003 Helber et al.
6,767,979 B1 7/2004 Muir et al.
6,807,745 B2 10/2004 Orton
6,822,016 B2 11/2004 McCabe et al.
6,867,245 B2 3/2005 Iwata et al.
6,918,931 B2 7/2005 Lai et al.
6,943,203 B2 9/2005 Vanderlaan et al.
6,951,894 B1 10/2005 Nicolson et al.
7,033,391 B2 4/2006 Lai et al.
7,052,131 B2 5/2006 McCabe et al.
7,247,692 B2 7/2007 Laredo
7,249,848 B2 7/2007 Laredo et al.
7,276,544 B2 10/2007 Lai et al.
7,396,890 B2 7/2008 Zanini et al.
7,461,937 B2 12/2008 STeffen et al.
7,468,398 B2 12/2008 Nicolson et al.
7,538,146 B2 5/2009 Nicolson et al.
7,553,860 B2 6/2009 Old
7,553,880 B2 6/2009 Nicolson et al.
7,572,841 B2 8/2009 Chen et al.
7,666,921 B2 2/2010 McCabe et al.
7,691,916 B2 4/2010 McCabe et al.
7,691,918 B2 4/2010 Jinkerson et al.
7,728,051 B2 6/2010 Weinschenk, III et al.
7,781,571 B2 8/2010 Weinschenk et al.
7,786,185 B2 8/2010 Rathore et al.
7,803,359 B1 9/2010 Jinkerson et al.
7,825,170 B2 11/2010 Steffen et al.
7,915,323 B2 3/2011 Awasthi et al.
7,934,830 B2 5/2011 Blackwell et al.
7,956,131 B2 6/2011 Arnold et al.
7,994,356 B2 8/2011 Awasthi et al.
8,022,158 B2 9/2011 Rathore et al.
8,026,326 B2 9/2011 Benz et al.
8,043,607 B2 10/2011 Jinkerson
8,113,655 B1 2/2012 Tyrin et al.
8,138,290 B2 3/2012 Blackwell et al.
8,153,703 B2 * 4/2012 Laredo ................ C07D 249/18
526/263
8,163,206 B2 4/2012 Chang et al.
8,207,244 B2 6/2012 Laredo
8,236,053 B1 8/2012 Freeman
8,262,947 B2 9/2012 Laredo
8,262,948 B2 9/2012 Laredo et al.
8,273,802 B2 9/2012 Laredo et al.
8,323,631 B2 12/2012 Jinkerson
8,329,775 B2 12/2012 Laredo
8,360,574 B2 1/2013 Ishak et al.
8,389,597 B2 3/2013 Blackwell et al.
8,399,538 B2 3/2013 Steffen et al.
8,415,404 B2 4/2013 Nicolson et al.
8,420,711 B2 4/2013 Awasthi et al.
8,450,387 B2 5/2013 McCabe et al.
8,470,906 B2 6/2013 Rathore et al.
8,476,390 B2 7/2013 Benz et al.
8,487,058 B2 7/2013 Liu et al.
8,507,577 B2 8/2013 Zanini et al.
8,568,626 B2 10/2013 Nicolson et al.
8,585,938 B1 11/2013 Jinkerson et al.
8,618,323 B2 12/2013 Benz et al.
8,637,621 B2 1/2014 Iwata et al.
8,697,770 B2 4/2014 Duis et al.
8,703,891 B2 4/2014 Broad
8,784,867 B2 7/2014 Samuel et al.
8,807,745 B2 8/2014 Nunez et al.
8,940,812 B2 1/2015 Reboul et al.
8,980,972 B2 3/2015 Driver
9,005,700 B2 4/2015 Bothe et al.
9,056,878 B2 6/2015 Fujisawa et al.
9,057,821 B2 6/2015 Broad et al.
9,125,829 B2 9/2015 Bonda et al.
9,145,383 B2 9/2015 Bonda et al.
9,170,349 B2 10/2015 Mahadevan et al.
9,217,813 B2 12/2015 Liu et al.
9,244,196 B2 1/2016 Scales et al.
9,249,249 B2 2/2016 Awasthi et al.
9,260,544 B2 2/2016 Rathore et al.
9,278,949 B2 3/2016 Loccufier
9,297,928 B2 3/2016 Molock et al.
9,297,929 B2 3/2016 Scales et al.
9,315,669 B2 4/2016 Holland et al.
9,611,246 B2 4/2017 Bonda et al.
9,637,444 B2 5/2017 Qian
9,667,800 B2 5/2017 Rodriguez et al.
9,733,493 B2 8/2017 Wooley
9,765,051 B2 9/2017 Bonda et al.
9,867,800 B2 1/2018 Bonda et al.
9,926,289 B2 3/2018 Bonda et al.
9,927,635 B2 3/2018 Ishak et al.
9,957,258 B2 5/2018 Kunimoto et al.
10,113,075 B2 10/2018 Nesvadba et al.
10,268,053 B2 4/2019 Holland et al.
10,338,408 B2 7/2019 Bothe et al.
10,597,515 B2 3/2020 Nesvadba et al.
10,845,625 B2 11/2020 Carrega et al.
10,935,695 B2 3/2021 Mahadevan et al.
11,401,400 B2 8/2022 Shishino et al.
11,543,683 B2 1/2023 Mahadevan et al.
11,820,899 B2 11/2023 Mahadevan et al.
11,993,037 B1 5/2024 Mahadevan et al.
2002/0042653 A1 4/2002 Copeland et al.
2004/0070726 A1 4/2004 Ishak
2005/0018131 A1 1/2005 Ishak
2005/0055090 A1 3/2005 Lai et al.
2005/0055091 A1 3/2005 Lai et al.
2005/0243272 A1 11/2005 Mainster et al.
2005/0254003 A1 11/2005 Jani et al.
2006/0092374 A1 5/2006 Ishak
2006/0252850 A1 11/2006 Jani et al.
2007/0092830 A1 4/2007 Lai et al.
2007/0092831 A1 4/2007 Lai et al.
2007/0100018 A1 5/2007 Hagting et al.
2007/0216861 A1 9/2007 Ishak et al.
2008/0002147 A1 1/2008 Haywood et al.
2008/0221674 A1 9/2008 Blum et al.
2010/0048847 A1 2/2010 Broad
2010/0113641 A1 5/2010 Laredo
2010/0168359 A1 7/2010 Domschke et al.
2010/0321632 A1 12/2010 Sanger
2011/0245818 A1 10/2011 Weinschenk, III
2011/0249234 A1 10/2011 Duis et al.
2012/0010703 A1 1/2012 Paul et al.
2012/0053313 A1 3/2012 Higgs et al.
2012/0196951 A1 8/2012 Mentak
2012/0262792 A1 10/2012 Goldberg et al.
2013/0009059 A1 1/2013 Caruso
2013/0057824 A1 3/2013 Harding et al.
2013/0095235 A1 4/2013 Bothe et al.
2013/0158150 A1 6/2013 Zhang et al.
2013/0168617 A1 7/2013 Alli et al.
2013/0172440 A1 7/2013 Alll et al.
2013/0217620 A1 8/2013 Alll et al.
2014/0024791 A1 1/2014 Alli et al.
2014/0031447 A1 1/2014 Alli et al.
2014/0044654 A1 2/2014 Bonda et al.
2014/0050681 A1 2/2014 Bonda et al.
2014/0093661 A1 4/2014 Trajkovska et al.
2014/0178595 A1 6/2014 Bothe et al.

(56) References Cited

U.S. PATENT DOCUMENTS

| | | | |
|---|---|---|---|
| 2014/0300857 | A1 | 10/2014 | Cohen-tannoudji et al. |
| 2015/0092155 | A1 | 4/2015 | Chang et al. |
| 2015/0094395 | A1 | 4/2015 | Alll et al. |
| 2015/0164852 | A1 | 6/2015 | Bonda et al. |
| 2015/0175732 | A1 | 6/2015 | Awasthi et al. |
| 2015/0316688 | A1 | 11/2015 | Cefalo et al. |
| 2016/0002200 | A1 | 1/2016 | Bonda et al. |
| 2016/0022555 | A1 | 1/2016 | Bonda et al. |
| 2016/0170093 | A1 | 6/2016 | Laredo et al. |
| 2017/0038605 | A1 | 2/2017 | Legerton |
| 2017/0075137 | A1 | 3/2017 | Lin et al. |
| 2017/0131574 | A1 | 5/2017 | Lee |
| 2017/0184878 | A1 | 6/2017 | Duis et al. |
| 2017/0227790 | A1 | 8/2017 | Lin et al. |
| 2017/0261768 | A1 | 9/2017 | Ambler et al. |
| 2018/0037690 | A1 | 2/2018 | Aitken et al. |
| 2018/0164608 | A1 | 6/2018 | Schmeder et al. |
| 2018/0208583 | A1 | 7/2018 | Kunimoto et al. |
| 2018/0263951 | A1 | 9/2018 | Bonda et al. |
| 2018/0371139 | A1 | 12/2018 | Mahadevan et al. |
| 2019/0002415 | A1 | 1/2019 | Mahadevan et al. |
| 2019/0002459 | A1 | 1/2019 | Mahadevan et al. |
| 2019/0121162 | A1 | 4/2019 | Alli et al. |
| 2019/0169438 | A1 | 6/2019 | Fromentin et al. |
| 2019/0179170 | A1 | 6/2019 | Chang |
| 2019/0271798 | A1 | 9/2019 | Mahadevan et al. |
| 2019/0271861 | A1 | 9/2019 | Hose |
| 2020/0347166 | A1 | 11/2020 | Alli et al. |
| 2020/0347167 | A1 | 11/2020 | Alli et al. |
| 2020/0399429 | A1 | 12/2020 | Alli et al. |
| 2020/0407324 | A1 | 12/2020 | Mahadevan et al. |
| 2020/0407337 | A1 | 12/2020 | Mahadevan |
| 2021/0061934 | A1 | 3/2021 | Martin et al. |
| 2022/0340759 | A1 | 10/2022 | Riederer et al. |
| 2022/0340760 | A1 | 10/2022 | Nankivil et al. |
| 2023/0066936 | A1 | 3/2023 | Buch et al. |
| 2023/0085695 | A1 | 3/2023 | Buch et al. |
| 2023/0117655 | A1 | 4/2023 | Mahadevan et al. |
| 2023/0288728 | A1 | 9/2023 | Mahadevan et al. |
| 2023/0296807 | A1 | 9/2023 | Aitken et al. |
| 2024/0067825 | A1 | 2/2024 | Mahadevan et al. |
| 2026/0003209 | A1 | 1/2026 | Martin et al. |

FOREIGN PATENT DOCUMENTS

| | | | |
|---|---|---|---|
| CN | 106366241 | A | 2/2017 |
| CN | 108586289 | A | 9/2018 |
| EP | 0080539 | B1 | 6/1983 |
| EP | 0131468 | B1 | 1/1985 |
| EP | 0924203 | A1 | 6/1999 |
| EP | 1870735 | A1 | 12/2007 |
| EP | 2123638 | A1 | 11/2009 |
| EP | 3052534 | B1 | 8/2016 |
| EP | 3419961 | A1 | 1/2019 |
| EP | 3419961 | B1 | 9/2020 |
| GB | 217810 | | 6/1924 |
| GB | 2319035 | A | 5/1998 |
| JP | H0743918 | A | 2/1995 |
| JP | 2004243596 | A | 9/2004 |
| JP | 2004277581 | | 10/2004 |
| JP | 200850463 | A | 3/2008 |
| JP | 4627009 | B2 | 2/2011 |
| JP | 2011219512 | A | 11/2011 |
| JP | 5544017 | B2 | 7/2014 |
| JP | 2015118122 | A | 6/2015 |
| JP | 2016133593 | A | 7/2016 |
| RU | 2175321 | C2 | 10/2001 |
| RU | 2196557 | C2 | 1/2003 |
| RU | 2197907 | C2 | 2/2003 |
| RU | 2294132 | C2 | 10/2006 |
| RU | 2466173 | C1 | 11/2012 |
| RU | 2481606 | C1 | 5/2013 |
| RU | 2540655 | C2 | 9/2014 |
| RU | 2557993 | C1 | 7/2015 |
| RU | 2577800 | C2 | 3/2016 |
| RU | 2628462 | C2 | 8/2017 |
| WO | 1999063366 | A1 | 12/1999 |
| WO | 2001030866 | A1 | 5/2001 |
| WO | 200212205 | A1 | 2/2002 |
| WO | 200242281 | A1 | 5/2002 |
| WO | 2003022321 | A2 | 3/2003 |
| WO | 2003089519 | A1 | 10/2003 |
| WO | 2007050395 | A2 | 5/2007 |
| WO | 2008061992 | A2 | 5/2008 |
| WO | 2011130139 | A1 | 10/2011 |
| WO | 2013055746 | A1 | 4/2013 |
| WO | 2013188825 | A1 | 12/2013 |
| WO | 2014018208 | A1 | 1/2014 |
| WO | 2014025370 | A1 | 2/2014 |
| WO | 2014026151 | A1 | 2/2014 |
| WO | 2015048035 | A1 | 4/2015 |
| WO | 2016100457 | A1 | 6/2016 |
| WO | 2016175619 | A1 | 11/2016 |
| WO | 2017/073467 | A1 | 5/2017 |
| WO | 2017106322 | A1 | 6/2017 |
| WO | 2019156143 | A1 | 8/2019 |
| WO | 2019166971 | A1 | 9/2019 |
| WO | 2020177534 | A1 | 9/2020 |
| WO | 2020261021 | A1 | 12/2020 |
| WO | 2020261091 | A1 | 12/2020 |
| WO | 2023242688 | A1 | 12/2023 |

OTHER PUBLICATIONS

PCT International Preliminary Report on Patentability, dated Mar. 1, 2022, for PCT Int'l Appln. No. PCT/IB2020/057733.

PCT International Search Report, dated Mar. 1, 2022, for PCT Int'l Appln. No. PCT/IB2021/061175.

Belikov, V.G., "The Relationship Between Chemical Structure, Properties of Substances and Their Effect on the Organism", Pharmaceutical Chemistry, pp. 27-29, 2007.

Dyson et al., "Chemistry of Synthetic Drugs Substances", Moscow: Mir, 18 pages, 1964.

Fadli et al., "Permeation and Pervaporation of Water through Contact Lens Materials", Johnson & Johnson Vision Care, Inc. Jacksonville, Fl, USA, 1 pages, 2016.

International Search Report and Written Opinion, received for PCT Application No. PCT/IB2018/053669, mailed on Jul. 17, 2018, 14 pages.

International Search Report and Written Opinion, received for PCT Application No. PCT/IB2018/054585, mailed on Nov. 9, 2018, 12 pages.

International Search Report and Written Opinion, received for PCT Application No. PCT/IB2018/054588, mailed on Oct. 4, 2018, 17 pages.

International Search Report and Written Opinion, received for PCT Application No. PCT/IB2023/055938, mailed on Oct. 18, 2023, 12 pages.

ISO 18369-3, "Ophthalmic Optics-Contact lenses", Measurement methods, Part 3, 44 pages, Aug. 15, 2006.

ISO 18369-4, "Ophthalmic Optics-Contact Lenses-Part 4: Physicochemical Properties of Contact Lens Materials", International Organization for Standardization, Aug. 15, 2006, 38 pages.

ISO 9913-1, "Optics and Optical Instruments—Contact Lenses—Part 1: Determination of Oxygen Permeability and Transmissibility by the FATT Method", International Organization for Standardization, Nov. 1, 1996, 16 pages.

Beatty et al., "Macular pigment and age related macular degeneration," Br. J. Ophthalmol. 1999, vol. 83, pp. 867-877.

Belusa, J. et al, 2-(2-Hydroxyphenyl)benzotriazoles. I. Synthesis and their ultraviolet and infrared spectra, Chem.zvesti 1974, vol. 28, No. 5, pp. 673-679.

Bernstein et al., "Lutein, zeaxanthin, and meso-zeaxanthin: The basic and clinical science underlying carotenoid-based nutritional interventions against ocular disease," Progress in Retinal and Eye Research, vol. 50, pp. 34-66, (2016).

Berthon, et al., Synthesis, Electrochemical and Spectroscopic Properties of Pendant Hydroquinone-and Quinone-Substitued Polypyridyl Ruthenium (11) Complex, Inorganica Chimica Acta, 1993, pp. 3-7, vol. 204.

(56) References Cited

OTHER PUBLICATIONS

Boon et al., "Factors Influencing the Chemical Stability of Carotenoids in Foods," Critical Reviews in Food Science and Nutrition, vol. 50, pp. 515-532 (2010).
Burton et al., "B-Carotene autoxidation: oxygen copolymerization, non-vitamin A products, and immunological activity," Can. J. Chem., vol. 92, pp. 305-316 (2014).
Chen et al., Dicyanomethylenated Acridone Based Crystals: Torsional Vibration Confinement Induced Emission with Supramolecular Structure Dependent and Stimuli Responsive Characteristics, The Journal of Physical Chemistry, 2016, 587-597, 120.
Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.
Crivello, et al., Photoinitiators for Free Radical Cationic & Anionic Photopolymerisation, 2nd Edition, vol. III, pp. 275-298, John Wiley and Sons, New York, 1998.
Doutch et al, Ultraviolet Light Transmission through the Human Corneal Stroma is Reduced in the Periphery, Biophysical Journal, vol. 102, Mar. 2012, pp. 1258-1264.
Hafez et al, Carbonyl and Thiocarbonyl Compounds. V. Synthesis of Newer Unsaturated Nitriles, Carboxylic Acids, and Esters Derived from Xanthene and Thiaxanthene, Journal of Organic Chemistry, vol. 26, pp. 3988-3991, Oct. 1961.
Ham et al., "Retinal sensitivity to damage from short wavelength light." Nature, vol. 260 (1976), pp. 153-155.
Hammond et al, Contralateral comparison of blue-filtering and non-blue-filtering intraocular lenses: glare disability, heterochromatic contrast, and photostress recovery, Clinical Ophthalmology, 2010, pp. 1465-1473, vol. 4, Dovepress, US.
International Conference on Harmonisation (ICH) of Technical Requirements for Registration of Pharmaceuticals for Human Use guideline, Q1B Photostability Testing of New Drug Substances and Products, published on Nov. 1996.
Jockusch et al, Photostabilization of Endogenous Porphyrins: Excited State Quenching by Fused Ring Cyanoacrylates, Photchemical & Photobiological Sciences, 2014, vol. 13, No. 8, pp. 1180-1184.
Johnston et al., "Biologically Active Polymers from Spontaneous Carotenoid Oxidation: A New Frontier in Carotenoid Activity," Plos One, vol. 9, Issue 10, pp. 1-10 (Oct. 2014).
Larn, et al., Synthesis of Dinucleating Phenanthroline-Based Ligands, Tetrahedron, Jul. 9, 1999, pp. 8377-8384, vol. 55 Issue 28.
Latif et al, Cleavage of Xanthene Ethers a New Route to 9-Substituted Xanthenes, Canadian Journal of Chemistry, vol. 42 (1964), pp. 1736-1740.
Luning, et al., Bimacrocylic 1,10-Phenanthroline Cyclophanes, Chemische Beri, 1990, pp. 643-645, vol. 123 Issue 3.
Nishino, et al., Manganese (111)-Mediated Carbon-Carbon Bond Formation in the Reaction of Xanthenes With Active Methylene Compounds, The journal of organic chemistry, Jan. 1, 1992, pp. 3551-3557, vol. 57.
PCT International Preliminary Report on Patentability, dated Sep. 8, 2020, for PCT Int'l Appin. No. PCT/IB2019/051582.
PCT International Preliminary Report on Patentability, dated Dec. 28, 2021, for PCT Int'l Appln. No. PCT/IB2020/055485.
PCT International Preliminary Report on Patentability, dated Dec. 28, 2021, for PCT Int'l Appln. No. PCT/IB2020/055868.
PCT International Search Report, dated Oct. 9, 2020, for PCT Int'l Appln. No. PCT/IB2020/057732.
PCT International Search Report, dated Oct. 9, 2020, for PCT Int'l Appln. No. PCT/IB2020/057733.
PCT International Search Report, dated Jul. 23, 2020, for PCT Int'l Appln. No. PCT/IB2020/055485.
PCT International Search Report, dated Sep. 23, 2020, for PCT Int'l Appln. No. PCT/IB2020/055868.
PCT International Search Report, dated May 24, 2019, for PCT Int'l Appln. No. PCT/IB2019/051582.
Reck, et al., Enantiopure Chiral Chiral Concave 1,10-Phenanthrolines, European Journal of Organic Chemistry, 2016, pp. 1119-1131, vol. 2016 Issue 6.
Ribeiro et al., "Antioxidant and pro-oxidant activities of carotenoids and their oxidation products," Food and Chemical Toxicology, vol. 120, pp. 681-699 (2018).
Sato, et al., Synthesis and characterization of electron transporting polymers having thioxanthene derivatives, Synthetic Metals, Jan. 1, 1999, pp. 55-60, vol. 105.
Selvam, et al., Tunable anchoring groups@acridone-linked triphenylamine based pendant chromophores and their effects on the photovoltaic performance as sensitizers for dye-sensitized solar cellst, RSC Advances, Jan. 1, 2016, pp. 109054-109060, vol. 6 Issue 110.
Statement on Ocular Ultraviolet Radiation Hazards in Sunlight, American Optometric Association, Nov. 10, 1993.
Stringham et al., "Macular Pigment and Visual Performance in Glare: Benefits for Photostress Recovery, Disability Glare, and Visual Discomfort," IOVS, Sep. 2011, vol. 52, No. 10, pp. 7406-7415.
Takeda et al., Anisotropic Dissociation of π-π Stacking and Flipping-Motion-Induced Crystal Jumping in Alkylacridones and Their Dicyanomethylene Derivatives, Chem. Eur. J., 2016, 7763-7770, 22.
Ty et al., "Oxidation and Thermal Degradation of Carotenoids," Journal of Oil Palm Research, vol. II, No. 1, pp. 62-78 (Jun. 1999).
Bondyreva E. Y., "Polimerization", Methodological Guidelines for Independent Work. Nizhnekamsk Chemical and Technological Institute of the Federal State Budget Educational Institution of Higher Professional Education "Kazan National Research Technological University", Nizhnekamsk, 2014, pp. 4-13.
Kolpashchikova et al., "Organic Chemistry" Part II. Arenes. Halogened Hydrocarbons. Ministry of Education of the Russian Federation. Yaroslavl State Technical University, 1999, p. 14.
Sutjagin et al., "Chemistry and Physics of Polymers," Training Manual. TPU Publishing House, Tomsk, 2003, Chapter 1, p. 9, Chapter 2, pp. 19-56.
PCT International Preliminary Report on Patentability, dated Jun. 13, 2023, for PCT Int'l Appln. No. PCT/IB2021/061175.
Liu, Zhuo., "Tutorial on Modern Rock and Mineral Analytic Experiments", Geological Press, p. 42, Oct. 31, 2015.
Chakrabarti et al., "Statistics of Real-World Hyperspectral Images", CVPR 2011, pp. 193-200, June 20-25, 2011.
Das et al., "In vitro and schematic model eye assessment of glare or positive dysphotopsia-type photic phenomena: comparison of a new material IOL to other monofocal IOLs", Journal of Cataract Refractive Surgery, vol. 45, Issue 2, pp. 219-227, Feb 2019.
Elsherif et al., "Contact Lenses for Color Vision Deficiency", Advanced Materials Technologies, vol. 6, Issue 1, pp. 1-9, Jan. 2021.
Foster et al., "Frequency of Metamerism in Natural Scenes", Journal of the Optical Society of America A, vol. 23, No. 10, pp. 2359-2372, Oct. 2006.
Harris et al., "Effect of Tinted Contact Lenses on Color Vision", Am J Optom Physiol Opt., vol. 53, No. 3, pp. 145-148, Mar. 1976.
Laxer, "Soft Tinted Contact Lenses and Color Discrimination", International Contact Lens Clinic, vol. 17, pp. 88-91, Mar.-Apr. 1990.
Macleod et al., "Chromaticity Diagram Showing Cone Excitation by Stimuli of Equal Luminance", Journal of the Optical Society of America, vol. 69, Issue 8, pp. 1183-1186, Aug. 1979.
Mencucci et al., "Visual Outcome, Optical Quality and Patients' Satisfaction with a New Monofocal Intraocular Lens, Enhanced for Intermediate Vision: Preliminary Results", Journal of Cataract and Refractive Surgery, vol. 46, Issue 3, pp. 378-387, Mar. 2020.
Miao et al., "Objective Optical Quality and Intraocular Scattering in Myopic Adults", Investigative Ophthalmology & Visual Science, vol. 55, No. 9, pp. 5582-5587, Sep. 2014.
Mostafa et al., "The Effect of Age and Gender on Tear Film Breakup Time", In Egyptian Journal of Medical Research, vol. 2, Issue 2, 11 pages, 2021.

(56) References Cited

OTHER PUBLICATIONS

Nascimento et al., "Statistics of Spatial Cone-excitation Ratios in Natural Scenes", Journal of the Optical Society of America A, vol. 19, Issue 8, pp. 1484-1490, Aug. 2002.
Parraga et al., "Color and Luminance Information in Natural Scenes", Journal of the Optical Society of America A, vol. 15, No. 3, pp. 563-569, Mar. 1998.
Patel, et al., "Effect of Visual Display Unit Use on Blink Rate and Tear Stability", In Optom Visual Sci, vol. 68, Issue 11, pp. 888-892, Nov. 1991.
Pokorny et al., "Aging of the Human Lens", Applied Optics, vol. 26, No. 8, pp. 1437-1440, Apr. 1987.
Stockman et al., "The Spectral Sensitivities of the Middle- and Long-wavelength-sensitive Cones Derived from Measurements in Observers of Known Genotype", Vision Research, vol. 40, pp. 1711-1737, 2000.
Tan et al., "Dynamic Change of Optical Quality in Patients with Dry Eye Disease", In Invest Ophthalmol Vis Sci. vol. 56, Issue 5, pp. 2848-2854, May 2015.
Tester et al., "Dysphotopsia in phakic and pseudophakic patients: incidence and relation to intraocular lens type", In Journal of Cataract Refractive Surgery, vol. 26, Issue 6 , pp. 810-816, Jun. 2000.
Tsubota et al., "Dry Eyes and Video Display Terminals", In New England Journal of Medicine, vol. 328, Issue 8, p. 584, Feb. 25, 1993.
Van den Berg, T. J. T. P., "Importance of Pathological Intraocular Light Scatter for Visual Disability", In Documenta Ophthalmologica, vol. 61, pp. 327-333, 1986.
Xi et al., "Assessment of Tear Film Optical Quality in a Young Short Tear Break-up Time Dry Eye: Case-control study", Medicine, vol. 98, Issue 40, pp. 1-6, 2019.
US Unpublished Patent, U.S. Appl. No. 18/871,664, filed Dec. 4, 2024, 103 pages.
Krick et al. "Temperature—DependentDynamics of Push—Pull Rotor SystemsBased on Acridinylidene CyanoaceticEsters", European Journal of Organic Chemistry, pp. 5141-5146, Jul. 26, 2017.
Ma et al., "Studies on K2CO3—Catalyzed 1,4—Addition of 1,2—Allenic Ketones with Diethyl Malonate: Controlled Selective Synthesis of β, γ—Unsaturated Enones and α-Pyrones", Journal of Organic Chemistry, vol. 68, pp. 8996-9002, Oct. 24, 2003.
Maas et al., "Dication Ethers-10. Stable Dipoles from A Bis-Acridinium Ether Salt and Cyclic Beta-Diketonates", Tetrahedron, vol. 41, No. 20, pp. 4529-4536, 1985.

* cited by examiner

PHOTOSTABLE MIMICS OF MACULAR PIGMENT

RELATED APPLICATIONS

This application claims priority to U.S. Provisional Patent Application Ser. No. 63/127,382, filed Dec. 18, 2020, which is incorporated herein by reference in its entirety.

FIELD OF THE INVENTION

The invention relates to visible light absorbers. More particularly, the invention relates to compounds that substantially mimic the visible light absorbance properties of macular pigment while remaining photostable. The compounds may be used in a variety of articles, including ophthalmic devices.

BACKGROUND OF THE INVENTION

Human ocular tissues contain the dietary carotenoids lutein (L) and zeaxanthin (Z), collectively known as macular pigment (MP). Several reports describe the benefits of MP, for instance as a short-wavelength (blue light) filter and as a powerful antioxidant, have been made. MP is also believed to play a protective role against age related macular degeneration (AMD) (Bernstein, P. S., Li, B., Vachali, P. P., Gorusupudi, A., Shyam, R., Henriksen, B. S., Nolan, J. M. Prog. Retin. Eye Res. 2016, 50, 34-66; Beatty, S., Boulton, M., Koh, H-H., Murray, I, J. *Br. J. Ophthalmol* 1999, 83, 867-877). Macular pigment has further been found to correlate significantly with photostress recovery times, reduced disability glare contrast thresholds, and reduced visual discomfort (Stringham, J. M., Garcia., P. V., Smith, P. A., McLin, L, N., Foutch, B. K. *IOVS,* 2011, 52 (10) 7406-7415).

The chemical entities associated with macular pigment are carotenoid derivatives that possess extensive unsaturation and are highly reactive toward olefin isomerization and oxidation upon photoexcitation. The antioxidant protective mechanism that carotenoids provide is essentially sacrificial, where excitation of the pi system results in the reaction of its excited state with triplet oxygen, thereby protecting/limiting the excitation and reactions of other photosensitive compounds in the ocular environment. See e.g., Ribeiro, et al., Food and Chemical Toxicology, Vol. 120, pp. 681-699 (2018); Burton, et al., Can. J. Chem., Vol. 92, pp. 305-316 (2014); Ty, et al., Journal of Oil Palm Research Vol. II No. 1, pp. 62-78 (June 1999); Johnston, et al., Plos One, Vol. 9 (10), pp. 1-10 (2014); and Boon, et al., Critical Reviews in Food Science and Nutrition, Vol. 50, pp. 515-532 (2010).

While the incorporation of macular pigment into products for the purpose of offering ocular protection is desirable, the overall lack of stability (thermal, oxidative, and photochemical) of carotenoids creates a very high barrier to the development of such products. Thus, it would be a significant advance if new stable materials that mimic the light absorbing properties of macular pigment were developed.

SUMMARY OF THE INVENTION

The invention relates to compounds that absorb light in the 400 to 500 nm wavelength range and possess absorption spectra that substantially mimic that of the macular pigment. Such compounds are also photostable, for instance when measured for changes/loss of absorption characteristics upon exposure to conditions analogous to those described in ICH Q1B. In addition, compounds may exhibit a high extinction coefficient at desired wavelengths in the 400 to 500 nm range and may therefore be used in low concentrations to provide their light absorbing benefits. Further, the compounds are thermally stable. The compounds described herein may, for instance, be used in ophthalmic devices to, for example, supplement the macular pigment optical density (MPOD) of wearers.

Accordingly, in one aspect the invention provides a compound having a visible light absorption maximum between 430 and 480 nm and a full width half maximum (FWHM) at the visible light absorption maximum of at least 35 nm and up to 150 nanometers, preferably up to 100 nanometers, wherein the compound is photostable. The compound may exhibit a molar extinction coefficient of at least 7740 $L \cdot mol^{-1} \cdot cm^{-1}$.

In another aspect, the invention provides a compound having a visible light absorption maximum between 430 and 480 nm and a full width half maximum (FWHM) at the visible light absorption maximum of at least 35 nm and up to 150 nanometers, preferably up to 100 nanometers, wherein the compound is more photostable than macular pigment. The compound may exhibit a molar extinction coefficient of at least 7740 $L \cdot mol^{-1} \cdot cm^{-1}$.

In a further aspect, the invention provides a compound having a visible light absorption maximum between 430 and 480 nm and a full width half maximum (FWHM) at the visible light absorption maximum of at least 35 nm and up to 150 nanometers, preferably up to 100 nanometers, wherein the compound is thermally stable. The compound may exhibit a molar extinction coefficient of at least 7740 $L \cdot mol^{-1} \cdot cm^{-1}$.

In another aspect, the invention provides a compound having a visible light absorption maximum between 430 and 480 nm and a full width half maximum (FWHM) at the visible light absorption maximum of at least 35 nm and up to 150 nanometers, preferably up to 100 nanometers, wherein the compound is more thermally stable than macular pigment. The compound may exhibit a molar extinction coefficient of at least 7740 $L \cdot mol^{-1} \cdot cm^{-1}$.

In a further aspect, the invention provides a compound comprising a chromophore, the chromophore having a substructure of formula I:

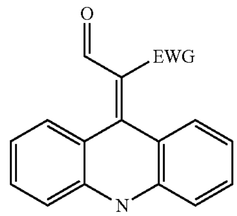

(I)

wherein EWG is an electron withdrawing group. The compound may exhibit a visible light absorbance maximum in the range of 440 to 480 nm, or 450 to 475 nm or 460 to 470 nm.

In a still further aspect, the invention provides an ophthalmic device comprising a compound as described herein.

In a yet further aspect, the invention provides a method for making compounds as described herein.

DETAILED DESCRIPTION OF THE INVENTION

Figure 1:
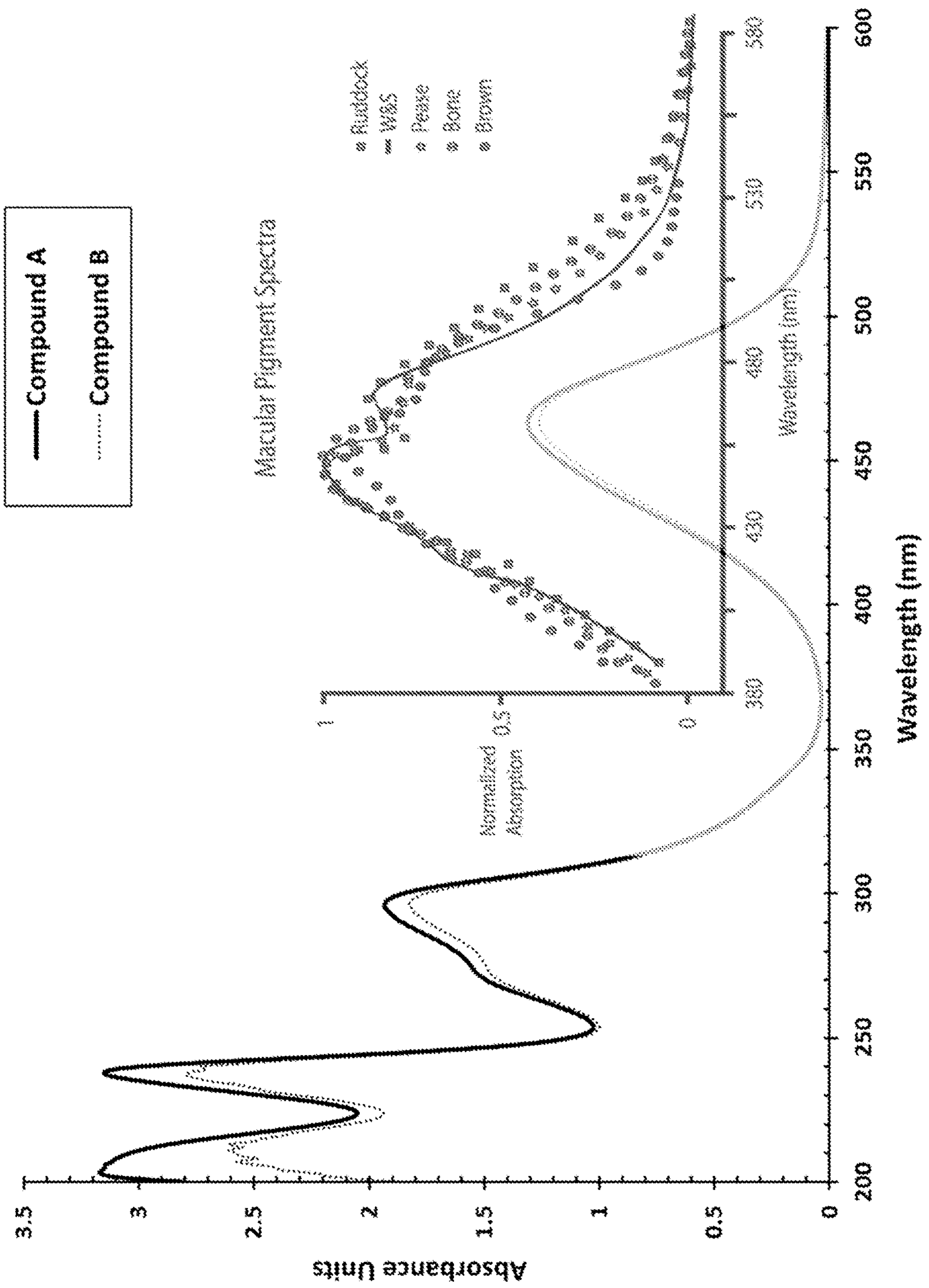
FIG. 1 shows UV-VIS absorbance spectra of 0.1 mM methanolic solutions of Compound A and Compound B of the invention, superimposed on the literature spectrum of macular pigment.

It is to be understood that the invention is not limited to the details of construction or process steps set forth in the following description. The invention is capable of other embodiments and of being practiced or being carried out in various ways using the teaching herein.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula [***]n, is used to depict the number of repeating units in a polymer's chemical formula, the formula should be interpreted to represent the number average molecular weight of the macromolecule.

The term "individual" includes humans and vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any optical device relating to the eye and includes devices which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include spectacle lenses, sunglass lenses, soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

Spectacle lenses or sunglasses may be comprised of mineral material, for example based on silicate, or made from an organic material, such as polycarbonate; polyamide; polyimide; polysulfones; polyethylene terephthalate/polycarbonate copolymers; and various other materials known in the art.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, preferably free radical polymerization, for example a carbon-carbon double bond which can polymerize when subjected to radical polymerization initiation conditions. Non-limiting examples of polymerizable groups include (meth)acrylates, styryls, (meth)acrylamides, and vinyl groups. Preferably, the polymerizable group is selected from (meth)acrylate, (meth)acrylamide, N-vinyl lactam, N-vinylamide, vinyl carbonate, vinyl ether, vinyl carbamate, and styryl functional groups. More preferably, the polymerizable group is selected from (meth)acrylates and (meth)acrylamides. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that may swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495,313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of suitable families of hydrophilic components that may be present in the reactive mixture include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof. Silicone-containing components are well known and have been extensively described in the patent literature. For instance, the silicone-containing component may comprise at least one polymerizable group (e.g., a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing), at least one siloxane group, and one or more linking groups (which may be a bond) connecting the polymerizable group(s) to the siloxane group(s). The silicone-containing components may, for instance, contain from 1 to 220 siloxane repeat units. The silicone-containing component may also contain at least one fluorine atom. Silicone hydrogel lenses may contain a coating, and the coating may be the same or different material from the substrate.

Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

"Reactive components" are the polymerizable compounds (such as monomers, macromers, oligomers, prepolymers, and cross-linkers) in the reactive mixture (defined below), as well as any other components in the reactive mixture which are intended to substantially remain in the resultant polymeric network after polymerization and all work-up steps (such as extraction steps) and packaging steps have been completed. Reactive components may be retained in the polymeric network by covalent bonding, hydrogen bonding, electrostatic interactions, the formation of interpenetrating polymeric networks, or any other means. Components that are intended to release from the polymeric network once it is in use are still considered "reactive components." For example, pharmaceutical or nutraceutical components in a contact lens which are intended to be released during wear are considered "reactive components." Components that are intended to be removed from the polymeric network during the manufacturing process (e.g., by extraction), such as diluents, are not "reactive components."

The terms "reactive mixture" and "reactive monomer mixture" refer to the mixture of components which are mixed together and, when subjected to polymerization conditions, result in formation of a polymeric network (such as conventional or silicone hydrogels) as well as biomedical devices, ophthalmic devices, and contact lenses made therefrom. The reactive mixture may comprise reactive components such as monomers, macromers, prepolymers, cross-linkers, and initiators, additives such as wetting agents, polymers, dyes, light absorbing compounds such as UV absorbers, pigments, photochromic compounds, pharmaceutical compounds, and/or nutraceutical compounds, any of which may be polymerizable or non-polymerizable but are capable of being retained within the resulting biomedical device (e.g., contact lens). The reactive mixture may also contain other components which are intended to be removed from the device prior to its use, such as diluents. It will be appreciated that a wide range of additives may be added based upon the contact lens which is made and its intended use. Concentrations of components of the reactive mixture are expressed as weight percentages of all reactive components in the reactive mixture, therefore excluding diluents. When diluents are used, their concentrations are expressed as weight percentages based upon the amount of all components in the reactive mixture (including the diluent).

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as $—CH_2—$, $—CH_2CH_2—$, $—CH_2CH_2CH_2—$, $—CH_2CH(CH_3)CH_2—$, and $—CH_2CH_2CH_2CH_2—$.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as $—CF_3—$ or $—CF_2CF_3—$. "Haloalkylene" means a divalent haloalkyl group, such as $—CH_2CF_2—$.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as $—CH_2CH_2NH—$.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., $—[Si—O]_n—$, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si—$ and "siloxy" refers to a structure of formula $R_3Si—O—$, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula $-(\text{alkylene-O})_p—$ or $—(\text{O-alkylene})_p-$, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., $HO—[CH_2CH_2O]_p—$ or $CH_3O—[CH_2CH_2O]_p—$). Examples of alkyleneoxy include polyethyleneoxy, polypropyleneoxy, polybutyleneoxy, and poly(ethyleneoxy-co-propyleneoxy).

"Oxaalkylene" refers to an alkylene group as defined above where one or more non-adjacent $CH_2$ groups have been substituted with an oxygen atom, such as $—CH_2CH_2OCH(CH_3)CH_2—$. "Thiaalkylene" refers to an alkylene group as defined above where one or more non-adjacent $CH_2$ groups have been substituted with a sulfur atom, such as $—CH_2CH_2SCH(CH_3)CH_2—$.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester ($—CO_2—$), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., $—OCF_2—$, $—OCF_2CF_2—$, $—OCF_2CH_2—$), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include $C_1$-$C_8$ alkylene (preferably $C_2$-$C_6$ alkylene), $C_1$-$C_8$ oxaalkylene (preferably $C_2$-$C_6$ oxaalkylene), $C_1$-$C_8$ thiaalkylene, $C_1$-$C_8$ alkylene-carboxylate-$C_1$-$C_8$ alkylene, $C_1$-$C_8$ alkylene-amide-$C_1$-$C_8$ alkylene, and $C_1$-$C_8$ alkylene-amine-$C_1$-$C_8$ alkylene, each of which is optionally substituted with 1 or 2 groups independently selected from hydroxyl and siloxy.

When the linking group is comprised of combinations of moieties as described above (e.g., alkylene and cycloalkylene), the moieties may be present in any order. For instance, if in Formula A below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula A, L is indicated as being alkylene-cycloalkylene, then Rg-L is preferably Rg-alkylene-cycloalkylene-.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "light absorbing compound" refers to a chemical material that absorbs light within the visible spectrum (e.g., in the 380 to 780 nm range). A "high energy radiation absorber," "UV/HEV absorber," or "high energy light absorbing compound" is a chemical material that absorbs various wavelengths of ultraviolet light, high energy visible light, or both. A material's ability to absorb certain wavelengths of light can be determined by measuring its UV/Vis transmission or absorbance spectrum.

When the compounds described herein contain olefinic double bonds or other centers of geometric asymmetry, and unless otherwise specified, it is intended that the compounds include the cis, trans, Z- and E-configurations. Likewise, all tautomeric and salt forms are also intended to be included.

The term "optional substituent" means that a hydrogen atom in the underlying moiety is optionally replaced by a substituent. Any substituent may be used that is sterically practical at the substitution site and is synthetically feasible. Identification of a suitable optional substituent is well within the capabilities of an ordinarily skilled artisan. Examples of an "optional substituent" include, without limitation, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^4R^5$, benzyl, $SO_3H$, $SO_3Na$, or —Y—$P_g$, wherein $R^4$ and $R^5$ are independently H or $C_1$-$C_6$ alkyl, Y is a linking group; and $P_g$ is a polymerizable group. The foregoing substituents may be optionally substituted by an optional substituent (which, unless otherwise indicated, is preferably not further substituted). For instance, alkyl may be substituted by halo (resulting, for instance, in $CF_3$).

"Substructure" means the chemical structure of the compound and any compounds derived from that chemical structure via the replacement of one or more hydrogen atoms by any other atom (which atom may be bound to other atoms or groups). Replacement, for instance, may be of one or more, preferably 1, 2, or 3, more preferably 1 or 2, more preferably 1, hydrogen atoms with an independently selected optional substituent. Encompassed within the definition of "substructure" are materials wherein the substructure forms a fragment of a larger compound, such as a monomer (e.g., containing one or more polymerizable groups), a polymer, or a macromolecule.

"Visible light absorption maximum" means a wavelength in the visible light wavelength range (380 to 760 nm) at which a light absorbance is a maximum. The definition encompasses materials that exhibit overall absorption maxima outside of the visible light range, such as within the UV region.

The terms "photostable," "photostability," or similar expressions mean that the compound (which may, when measured, be optionally embedded in an ophthalmic device, such as a hydrogel contact lens, and optionally measured either within or outside of a blister pack or a vial) exhibits a loss of absorbance at the visible light absorbance maximum of no more than 20 percent after exposure to light under conditions such as those of the International Conference on Harmonisation (ICH) of Technical Requirements for Registration of Pharmaceuticals for Human Use guideline, Q1B Photostability Testing of New Drug Substances and Products, published on November 1996. Preferably, the exposure is conducted under the ICH Photostability Guideline using an Option 2 light source with an estimated illuminance exposure of $1.5192\times10^6$ Lux hours (168.8 hours exposure time) and an estimated ultraviolet irradiation exposure of 259.4 Watt hours/$m^2$ (16.2 hours exposure time), preferably in a photostability chamber that is controlled at 25° C./Amb RH. After exposure, the UV/Vis spectrum of the sample is collected and compared to a sample's spectrum prior to exposure. Changes are calculated relative to the visible light absorbance maximum of the lens as observed prior to exposure. By way of example, if the absorbance at the visible light absorbance maximum before exposure is 4 absorbance units, and is 2 absorbance units after exposure, then the loss of absorbance is 50 percent. In the invention, the loss of absorbance after photo exposure is preferably no more than 15 percent, or no more than 10 percent, or no more than 7 percent, or no more than 5 percent, or no more than 4 percent, or no more than 3 percent, or no more than 2 percent, or no more than 1 percent, or no more than 0.5 percent, or no more than 0.1 percent.

The term "more photostable than macular pigment" or similar expression means that the compound (which may, when tested, be optionally embedded in an ophthalmic device, such as a hydrogel contact lens, and optionally measured either within or outside of a blister pack) exhibits less loss of absorbance at the visible light absorbance maximum than observed with macular pigment, following exposure to light, for instance under the ICH Photostability Guideline as described above.

The term full width half maximum (FWHM) means the width of the absorbance peak at half its maximum intensity.

The terms "thermally stable," "thermal stability," or similar expressions mean that the compound (which may, when measured, be optionally embedded in an ophthalmic device, such as a hydrogel contact lens, and optionally measured either within or outside of a blister pack or a vial) exhibits a loss of absorbance at the visible light absorbance maximum of no more than 20 percent after exposure in a stability chamber at 89° C. for one month as described in the examples below. After exposure, the UV/Vis spectrum of the sample is collected and compared to a sample's spectrum prior to exposure. Changes are calculated relative to the visible light absorbance maximum of the lens as observed prior to exposure. By way of example, if the absorbance at the visible light absorbance maximum before exposure is 4 absorbance units, and is 2 absorbance units after exposure, then the loss of absorbance is 50 percent. In the invention, the loss of absorbance after thermal exposure is preferably no more than 20 percent, or no more than 15 percent, or no more than 12 percent, or no more than 10 percent, or no more than 5 percent, or no more than 4 percent, or no more than 3 percent, or no more than 2 percent, or no more than 1 percent, or no more than 0.5 percent, or no more than 0.1 percent.

The term "more thermally stable than macular pigment" or similar expression means that the compound (which may, when tested, be optionally embedded in an ophthalmic device, such as a hydrogel contact lens, and optionally measured either within or outside of a blister pack) exhibits less loss of absorbance at the visible light absorbance maximum than observed with macular pigment, following thermal exposure as described above.

Unless otherwise indicated, ratios, percentages, parts, and the like are by weight.

Unless otherwise indicated, numeric ranges, for instance as in "from 2 to 10" or "between 2 and 10" are inclusive of the numbers defining the range (e.g., 2 and 10).

As noted above, in one aspect, the invention provides compounds that substantially mimic the visible light absorbance properties of macular pigment. The compounds are more photostable than macular pigment and may therefore be used in the manufacture of products. For instance, the compounds may be used in ophthalmic devices.

Thus, a compound of the invention may have a visible light absorption maximum that is between 430 and 480 nm and a full width half maximum (FWHM) at the visible light absorption maximum of at least 35 nm and up to 150 nanometers. The compound may be photostable (e.g., when measured according to ICH guideline Q1B). The compound may be more photostable than macular pigment.

The compound may have a visible light absorption maximum that is between 440 nm and 480 nm, or between 450 nm and 475 nm, or between 455 nm and 475 nm, or between 460 nm and 470 nm.

The compound may exhibit a FWHM at the visible light absorption maximum of at least 35 nm, or at least 40 nm, or at least 45 nm, or at least 55 nm, or at least 60 nm. The compound may exhibit a FWHM at the visible light absorption maximum of up to 125 nm, or up to 100 nm, or up to 95 nm, or up to 90 nm, or up to 85 nm, or up to 80 nm, or up to 75 nm, or up to 70 nm. The FWHM at the visible light absorption maximum may be in the range of 35 nm to 150 nm, or 35 nm to 100 nm, or 45 nm to 90 nm, or 55 nm to 80 nm, or 60 nm to 75 nm, or 60 nm to 70 nm, or 62 to 67 nm.

The compound of the invention may exhibit a molar extinction coefficient at the visible light absorption maximum of at least 5000, or at least 5500, or at least 6000, or at least 6500, or at least 7000, or at least 7500, or at least 7740, or at least 7800, or at least 8000, or at least 9000, or at least 10,000, or at least 11,000, or at least 12,000, or at least 12,500. Molar extinction coefficient is an intrinsic property of a material and may be calculated from absorbance data using the Beer-Lambert law. The unit is typically $L \cdot mol^{-1} \cdot cm^{-1}$.

The compound of the invention may comprise a chromophore having a substructure of formula I:

(I)

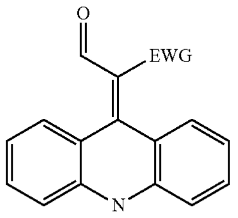

wherein EWG is an electron withdrawing group, the compound having a visible light absorbance maximum in the range of 440 to 480 nm, or 450 to 475 nm or 460 to 470 nm. EWG may be cyano, amide, ester, keto, or aldehyde. Preferably, EWG is cyano.

Compounds of the invention may be of formula II:

(II)

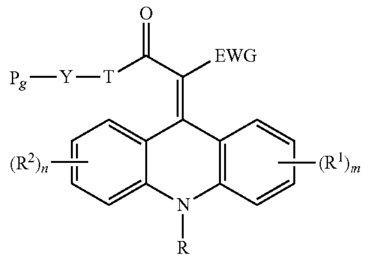

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

Compounds of formula II preferably contain one or two Y—$P_g$ groups. More preferably, the compounds contain one Y—$P_g$ group.

Compounds of formula II may include compounds of formula II-1, which are compounds of formula II wherein m and n are independently 0 or 1, or alternatively both are 0.

Compounds of formulae II and II-1 may include compounds of formula II-2, which are compounds of formula II or II-1 wherein n is 0 and m is 1.

Compounds of formulae II, II-1, and II-2 may include compounds of formula II-3, which are compounds of formula II, II-1, or II-2 wherein n is 0, m is 1, and $R^1$ is $C_1$-$C_6$ alkyl or $C_1$-$C_6$ alkoxy.

Compounds of formulae II, II-1, II-2, and II-3 may include compounds of formula II-4, which are compounds of formula II, II-1, II-2, or II-3 wherein R is H, or $C_1$-$C_6$ alkyl. Preferably, R is $C_1$-$C_6$ alkyl.

Compounds of formulae II, II-1, II-2, II-3 and II-4 may include compounds of formula II-5, which are compounds of formula II, II-1, II-2, II-3, or II-4 wherein T is $NR^6$, and $R^6$ is H or $C_1$-$C_6$ alkyl. Preferably, $R^6$ is H.

Compounds of formulae II, II-1, II-2, II-3, II-4, and II-5 may include compounds of formula II-6, which are compounds of formula II, II-1, II-2, II-3, II-4, or II-5 wherein $P_g$ (a polymerizable group) at each occurrence is independently styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making polymeric devices. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

Compounds of formulae II, II-1, II-2, II-3, II-4, II-5, and II-6 may include compounds of formula II-7, which are compounds of formula II, II-1, II-2, II-3, II-4, II-5, and II-6 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene ($—CH_2CH_2—$). When T in the compound of formula II is O, it is preferred that the carbon atom of the linking group to which the O is attached be hindered. For instance, if T is O and Y is alkylene, a preferred alkylene is $—C(R^H)_2(CH_2)_x—$, where $R^H$ is independently $C_1$-$C_6$ alkyl (preferably independently methyl or ethyl) and x is from 1 to 5.

Compounds of formulae II, II-1, II-2, II-3, II-4, II-5, II-6, and II-7 may include compounds of formula II-8, which are compounds of formula II, II-1, II-2, II-3, II-4, II-5, II-6, or II-7 wherein T is a bond or is $NR^6$ (preferably NH).

Compounds of formulae II, II-1, II-2, II-3, II-4, II-5, II-6, II-7, and II-8 may include compounds of formula II-9, which are compounds of formula II, II-1, II-2, II-3, II-4, II-5, II-6, II-7, or II-8, wherein EWG is cyano, amide, ester, keto, or aldehyde. Preferably, EWG is cyano.

Compounds of the invention may be of formula III:

(III)

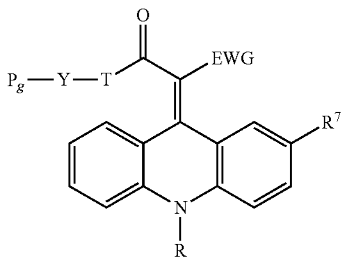

wherein:

T is a bond, O, or $NR^6$, wherein $R^6$ is H, $C_1$-$C_6$ alkyl, cycloalkyl, heterocycloalkyl, aryl, or heteroaryl;

R is H, $C_1$-$C_6$ alkyl, cycloalkyl, heterocycloalkyl, aryl, or heteroaryl;

Y is a linking group;

$P_g$ is a polymerizable group;

$R^7$ is H, $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl; and EWG is an electron withdrawing group.

Compounds of formula III may include compounds of formula III-1, which are compounds of formula III wherein $R^7$ is H.

Compounds of formulae III may include compounds of formula III-2, which are compounds of formula III wherein $R^7$ is $C_1$-$C_6$ alkyl, $C_1$-$C_6$ alkoxy, or $C_1$-$C_6$ thioalkyl.

Compounds of formulae III and III-2 may include compounds of formula III-3, which are compounds of formula III or III-2 wherein $R^7$ is $C_1$-$C_6$ alkoxy, such as ethoxy or methoxy, preferably methoxy.

Compounds of formulae III, III-1, 111-2, and III-3 may include compounds of formula III-4, which are compounds of formula III, III-1, III-2, or III-3 wherein R is H, or $C_1$-$C_6$ alkyl. Preferably, R is $C_1$-$C_6$ alkyl, such as methyl, ethyl, n-propyl, iso-propyl, n-butyl, t-butyl, or sec-butyl. Preferably, R is n-propyl or n-butyl.

Compounds of formulae III, III-1, III-2, III-3 and III-4 may include compounds of formula III-5, which are compounds of formula III, III-1, III-2, III-3, or III-4 wherein T is $NR^6$, and $R^6$ is H, or $C_1$-$C_6$ alkyl. Preferably, $R^6$ is H.

Compounds of formulae III, III-1, III-2, III-3, III-4, and III-5 may include compounds of formula III-6, which are compounds of formula III, III-1, III-2, III-3, III-4, or III-5 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. Preferred polymerizable groups include (meth)acrylate or (meth)acrylamide. A more preferred polymerizable group is methacrylate.

Compounds of formulae III, III-1, III-2, III-3, III-4, III-5, and III-6 may include compounds of formula III-7, which are compounds of formula III, III-1, III-2, III-3, III-4, III-5, and III-6 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene ($—CH_2CH_2—$). When T in the compound of formula III is O, it is preferred that the carbon atom of the linking group to which the O is attached be hindered. For instance, if T is O and Y is alkylene, a preferred alkylene is $—C(R^H)_2(CH_2)_x—$, where $R^H$ is independently $C_1$-$C_6$ alkyl (preferably independently methyl or ethyl) and x is from 1 to 5.

Compounds of formulae III, III-1, III-2, III-3, III-4, III-5, III-6, and III-7 may include compounds of formula III-8, which are compounds of formula III, III-1, III-2, III-3, III-4, III-5, III-6, or III-7 wherein T is a bond or is $NR^6$ (preferably NH).

Compounds of formulae III, III-1, III-2, III-3, III-4, III-5, III-6, III-7, and III-8 may include compounds of formula III-9, which are compounds of formula III, III-1, III-2, III-3, III-4, III-5, III-6, III-7, or III-8, wherein EWG is cyano, amide, ester, keto, or aldehyde. Preferably, EWG is cyano.

Specific examples of compounds of the invention are shown in Table A.

TABLE A

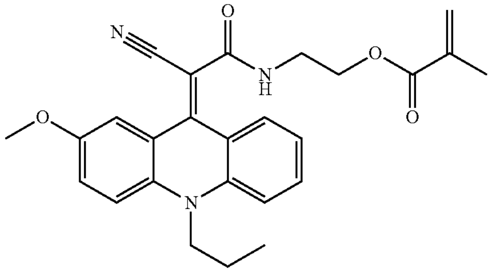 [SMILES: C=C(C)C(=O)OCCNC(=O)/C(C#N)=C1\c2ccccc2N(CCC)c2ccc(OC)cc21]

(E)-2-(2-cyano-2-(2-methoxy-10-propylacridin-9(10H)-ylidene)acetamido)ethyl methacrylate

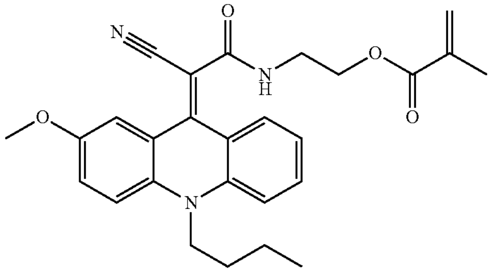 [SMILES: C=C(C)C(=O)OCCNC(=O)/C(C#N)=C1\c2ccccc2N(CCCC)c2ccc(OC)cc21]

(E)-2-(2-cyano-2-(2-methoxy-10-butylacridin-9(10H)-ylidene)acetamido)ethyl methacrylate Compounds of the invention may be prepared via Knoevenagel condensations of N-substituted acridones to form acridin-ylidene derivatives with active methylene derivatives. While condensation with malononitrile proceeds in the presence of a weaker electrophile such as acetic anhydride at elevated temperatures, reactions with weaker nucleophiles such as 2,4-diketones, 2-cyanoacetamide and 2-cyanoacetate derivatives may not form the desired products. Such transformations typically require strong Lewis acids such as titanium IV chloride, or a combination of strong electrophile such as thionyl chloride, and elevated temperatures to form reactive intermediates capable of undergoing the reaction. The known processes using titanium tetrachloride, or thionyl chloride at elevated temperatures require large excesses of the reagents and have poor selectivity and low yields of the desired products. Stoichiometric control of the electrophile and/or mild reaction conditions may help improve overall selectivity and product yields.

In one aspect of the invention, an improved method for synthesizing acridin-ylidene derivatives, such as the compounds described above, from N-substituted acridones is provided. The method utilizes triphenylphosphine dibromide. Triphenylphosphine dibromide maybe generated "in-situ" by the addition of bromine to triphenylphosphine in an appropriate solvent. Addition of an N-substituted acridone after the complete consumption of bromine avoids potential oxidation of the former and forms the desired product in high yields with significantly reduced byproduct formation. An exemplary synthesis for compounds of formula II is shown in Scheme A.

Scheme A

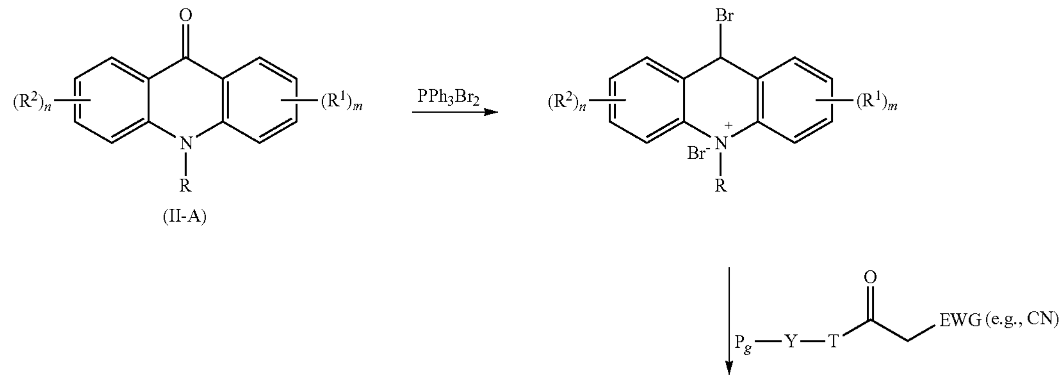

(II-A)

-continued

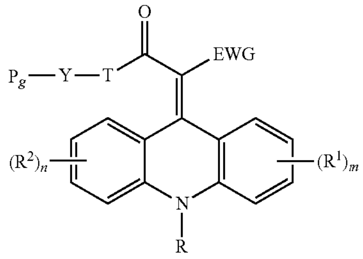

(II)

Compounds of the invention may be used in combination with other light absorbing compounds to provide desirable absorption characteristics. For example, preferred compositions may comprise a compound as described above together with a UV absorbing compound. Suitable UV absorbing compounds are known in the art and fall into several classes which include, but are not limited to, benzophenones, benzotriazoles, triazines, substituted acrylonitriles, salicyclic acid derivatives, benzoic acid derivatives, cinnamic acid derivatives, chalcone derivatives, dypnone derivatives, crotonic acid derivatives, or any mixtures thereof. A preferred class of UV absorbing compound is benzotriazoles, such as Norbloc (2-(2'-hydroxy-5-methacrylyloxyethylphenyl)-2H-benzotriazole).

Compounds of the invention may be included in reactive mixtures to form various products, including biomedical devices and ophthalmic devices. The compounds may, for instance, be incorporated within a device, and/or they may be coated on the surface of a device. When incorporated within a device, the compounds may generally be added to the reactive mixture from which the device is made and may be present in any amount up to the limit of their solubility. For instance, the compounds may be present at concentration of least 0.1 percent or at least 2 percent; and up to 10 percent or up to 5 percent, based on the weight percentages of all components in the reactive mixture, excluding diluent. A typical concentration may be in the range of 1 to 5 percent. The upper limit is typically determined by the solubility of the compound with other co-monomers and or diluents in the reactive monomer mix.

Preferably, the compounds of the invention are included in ophthalmic devices. A variety of ophthalmic devices may be prepared, including spectacles, sunglasses, hard contact lenses, soft contact lenses, corneal onlays, corneal inlays, intraocular lenses, or overlay lenses. Preferably, the ophthalmic device is an intraocular lens or a soft contact lens. The soft contact lens may be made from a conventional (non-silicone) hydrogel or from a silicone hydrogel.

Ophthalmic devices of the invention may comprise a free radical reaction product of a reactive mixture containing one or more monomers suitable for making the desired ophthalmic device (also referred to herein as device forming monomers or hydrogel forming monomers), and optional components. When polymerized, the reactive mixture results in formation of a polymeric network of which the ophthalmic device may be comprised. The polymeric network may, for instance, be a hydrogel (e.g., a conventional hydrogel or a silicone hydrogel).

A compound of the invention may be copolymerized with the other components in the reactive mixture, in which case the reactive mixture may, in addition to one or more monomers suitable for making the desired ophthalmic device (and any optional components), also contain one or more of the invention compounds.

Non-limiting examples of polymeric networks in which the invention compound may be incorporated (for instance, as a monomer) are described above and include, for instance, etafilcon, genfilcon, hilafilcon, lenefilcon, nesofilcon, omafilcon, polymacon, vifilcon, acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants.

By way of further example, a polymeric network may be made from a reactive mixture comprising one or more of: hydrophilic components, hydrophobic components, silicone-containing components, wetting agents such as polyamides, crosslinking agents, and further components such as diluents and initiators. As discussed above, the reactive mixture may also contain one or more inventive compounds.

Hydrophilic Components

Examples of suitable families of hydrophilic monomers that may be present in the reactive mixture include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl)(meth)acrylamide, N,N-bis(2-hydroxyethyl)(meth)acrylamide, N-(2-hydroxypropyl)(meth)acrylamide, N,N-bis(2-hydroxypropyl)(meth)acrylamide, N-(3-hydroxypropyl)(meth)acrylamide, N-(2-hydroxybutyl)(meth)acrylamide, N-(3-hydroxybutyl)(meth)acrylamide, N-(4-hydroxybutyl)(meth)acrylamide, 2-aminoethyl (meth)acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, or mixtures of the foregoing; one or more optionally repeating siloxane units; and one or more linking groups connecting the polymerizable groups to the siloxane units.

The silicone-containing component may comprise one or more polymerizable compounds of Formula A:

Formula A

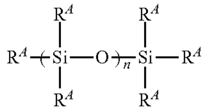

wherein:

at least one $R^A$ is a group of formula $R_g$-L- wherein $R_g$ is a polymerizable group and L is a linking group, and the remaining $R^A$ are each independently:

(a) $R_g$-L-, (b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof, (c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof, (d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof, (e) halo, (f) alkoxy, cyclic alkoxy, or aryloxy, (g) siloxy, (h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or (i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Examples of silicone-containing components suitable for use in the invention include, but are not limited to, compounds listed in Table B. Where the compounds in Table B contain polysiloxane groups, the number of SiO repeat units in such compounds, unless otherwise indicated, is preferably from 3 to 100, more preferably from 3 to 40, or still more preferably from 3 to 20.

TABLE B

| | |
|---|---|
| 1 | mono-methacryloxypropyl terminated mono-n-butyl terminated polydimethylsiloxanes (mPDMS) (preferably containing from 3 to 15 SiO repeating units) |
| 2 | mono-acryloxypropyl terminated mono-n-butyl terminated polydimethylsiloxane |
| 3 | mono(meth)acryloxypropyl terminated mono-n-methyl terminated polydimethylsiloxane |
| 4 | mono(meth)acryloxypropyl terminated mono-n-butyl terminated polydiethylsiloxane |
| 5 | mono(meth)acryloxypropyl terminated mono-n-methyl terminated polydiethylsiloxane |
| 6 | mono(meth)acrylamidoalkylpolydialkylsiloxanes |
| 7 | mono(meth)acryloxyalkyl terminated mono-alkyl polydiarylsiloxanes |
| 8 | 3-methacryloxypropyltris(trimethylsiloxy)silane (TRIS) |
| 9 | 3-methacryloxypropylbis(trimethylsiloxy)methylsilane |
| 10 | 3-methacryloxypropylpentamethyl disiloxane |
| 11 | mono(meth)acrylamidoalkylpolydialkylsiloxanes |
| 12 | mono(meth)acrylamidoalkyl polydimethylsiloxanes |
| 13 | N-(2,3-dihydroxypropane)-N'-(propyl tetra(dimethylsiloxy) dimethylbutylsilane)acrylamide |
| 14 | N-[3-tris(trimethylsiloxy)silyl]-propyl acrylamide (TRIS-Am) |
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |
| 17 | 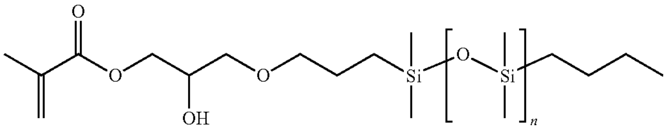 mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units) |
| 18 | 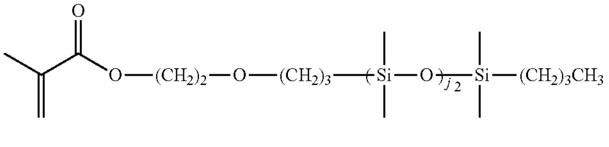 |
| 19 | 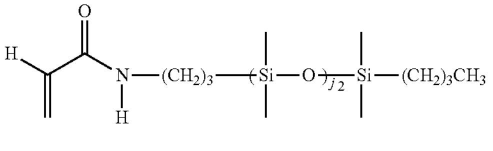 |

TABLE B-continued

| | |
|---|---|
| 20 | 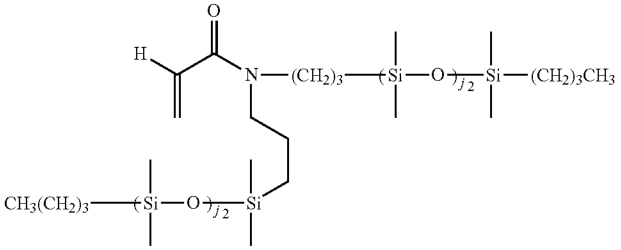 |
| 21 | 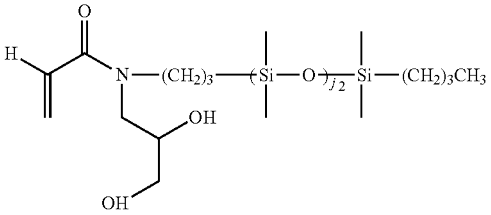 |
| 22 | 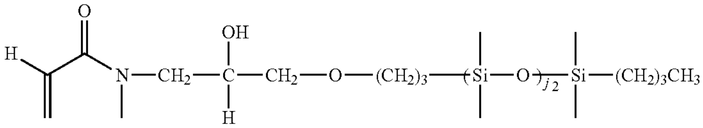 |
| 23 | 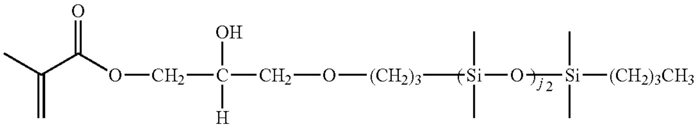 |
| 24 | 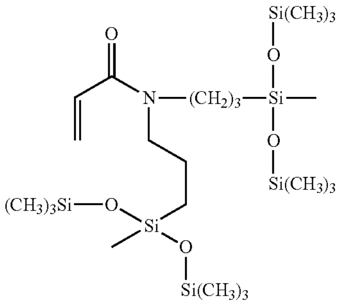 |

Additional non-limiting examples of suitable silicone-containing components are listed in Table C. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE C

| | |
|---|---|
| 25 | 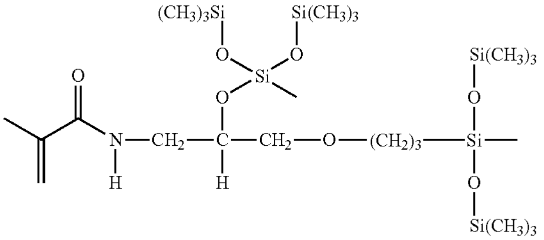 |

TABLE C-continued

26
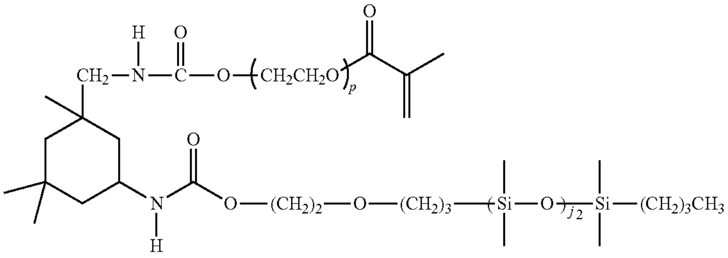

p is to 1 to 10

27
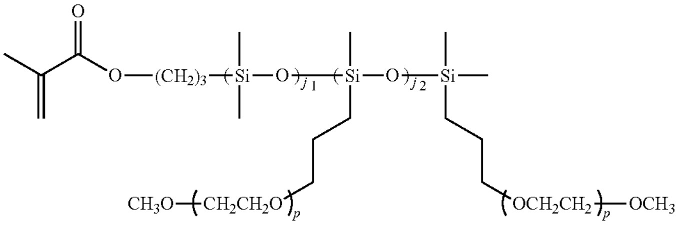

p is 5-10

28
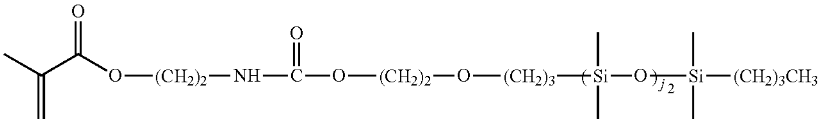

29
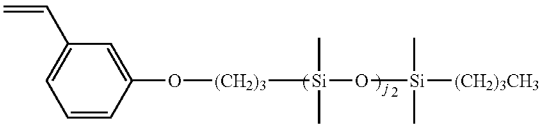

30 1,3-bis[4-(vinyloxycarbonyloxy)but-1-yl]tetramethyl-disiloxane
31 3-(vinyloxycarbonylthio) propyl-[tris (trimethylsiloxy)silane]
32 3-[tris(trimethylsiloxy)silyl]propyl allyl carbamate
33 3-[tris(trimethylsiloxy)silyl]propyl vinyl carbamate
34 tris(trimethylsiloxy)silylstyrene (Styryl-TRIS)

35
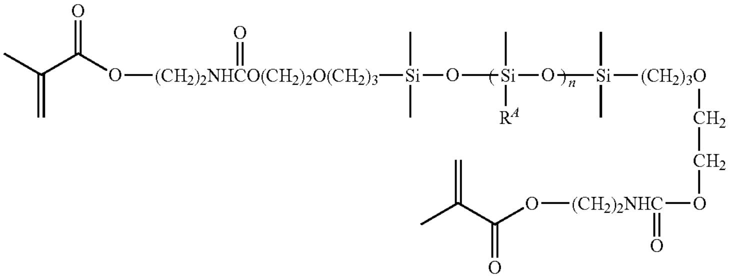

$R^A = CH_3$ (a) or $CH_2CH_2CF_2$ (b) or $CH_2—(CH_2)_2—$
$[OCH_2CH_2]_{1\text{-}10}—OCH_3$ (c); a + b + c = n 36
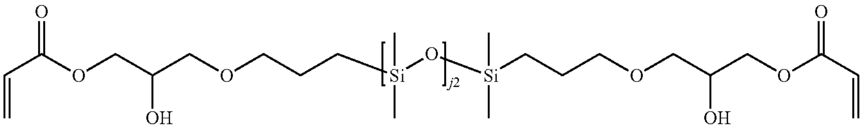

37
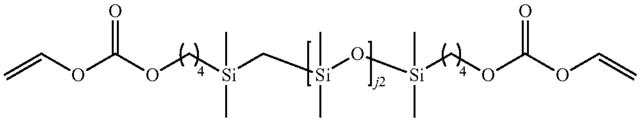

TABLE C-continued

38

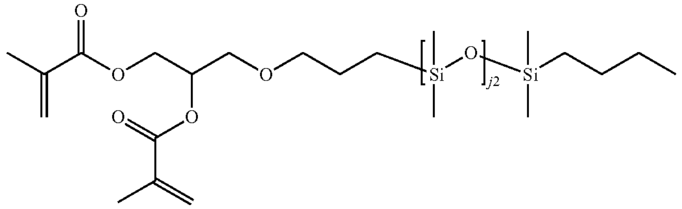

39

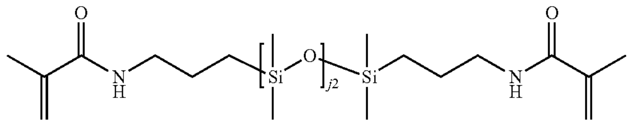

40

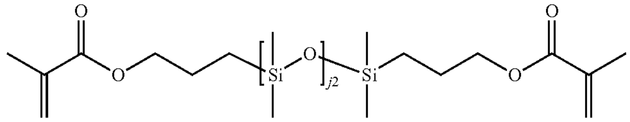

41

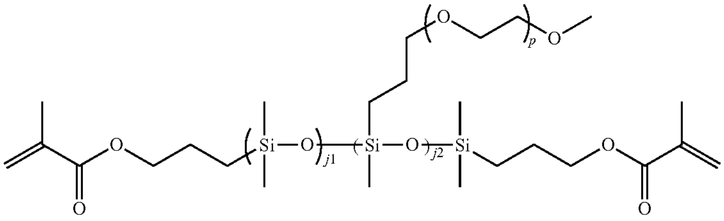

j1 = 80-90
j2 = 5-6
p = 7-8

42

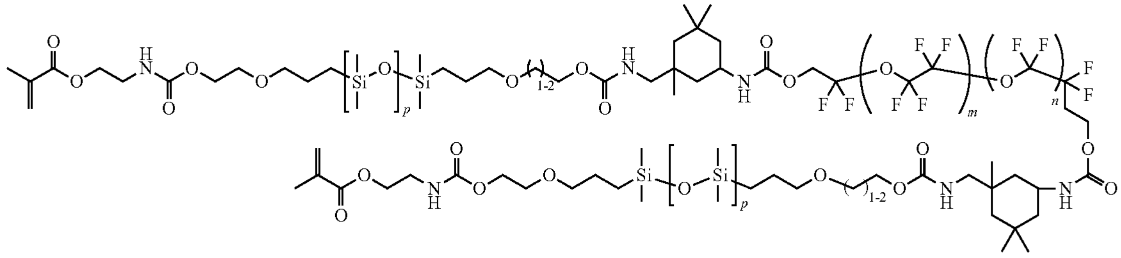

m ≈ 3.5-5.5; n ≈ 4-6.5; p ≈ 22-26

43

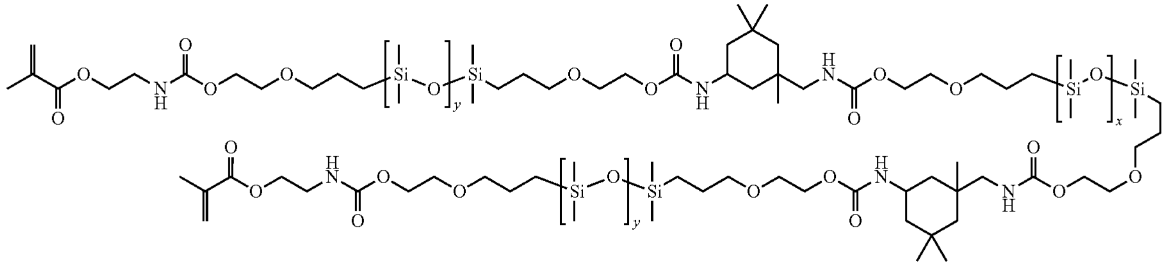

IEM-PDMS(Mn ≈ 3000)-IPDI-PDMS(Mn ≈ 2000)IPDI-PDMS(Mn ≈ 3000)-IEM (see WO2016100457)

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

Formula G1

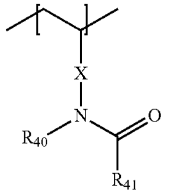

Formula G2

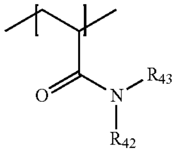

wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methyl-propionamide, N-vinyl-2-methyl-propionamide, N-vinyl-N, N'-dimethylurea, N, N-dimethylacrylamide, methacrylamide, and acyclic amides of Formulae G2 and G3:

Formula G2

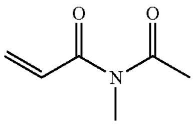

Formula G3

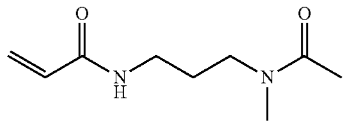

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

Formula G4

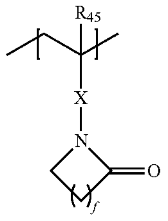

wherein R$_{45}$ is a hydrogen atom or methyl group; wherein f is a number from 1 to 10; wherein X is a direct bond, —(CO)—, or —(CONHR$_{46}$)—, wherein R$_{46}$ is a C$_1$ to C$_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes a, w-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described in Table D above.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, visibility tints, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine oxide (Irgacure 819), 2,4,6-trimethylbenzyldiphenyl phosphine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B.V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to an invention compound, any of the polymerizable compounds and optional components described above.

The reactive mixture may comprise: an invention compound, such as a compound of formula I, and a hydrophilic component.

The reactive mixture may comprise: an invention compound, such as a compound of formula I, and a hydrophilic component selected from DMA, NVP, HEMA, VMA, NVA, methacrylic acid, and mixtures thereof. Preferred are mixtures of HEMA and methacrylic acid.

The reactive mixture may comprise: an invention compound, such as a compound of formula I, a hydrophilic component, and a silicone-containing component.

The reactive mixture may comprise: an invention compound, such as a compound of formula I, a hydrophilic component selected from DMA, HEMA and mixtures thereof; a silicone-containing component selected from 2-hydroxy-3-[3-methyl-3,3-di(trimethylsiloxy)silyl-propoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof; and a wetting agent (preferably PVP or PVMA). For the hydrophilic component, mixtures of DMA and HEMA are preferred. For the silicone containing component, mixtures of SiMAA and mPDMS are preferred.

The reactive mixture may comprise: an invention compound, such as a compound of formula I, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

The reactive mixture may comprise: an invention compound, such as a compound of formula I; between about 1 and about 15 wt % at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g., OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first mono-functional, hydroxyl substituted poly(disubstituted siloxane) and the second hydroxyl substituted poly (disubstituted siloxane) are present in concentrations to provide a ratio of weight percent of the first mono-functional, hydroxyl substituted poly(disubstituted siloxane) to weight percent of the second hydroxyl substituted poly (disubstituted siloxane) of 0.4-1.3, or 0.4-1.0.

The foregoing reactive mixtures may contain optional ingredients such as, but not limited to, one or more initiators, internal wetting agents, crosslinkers, other UV or HEV absorbers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic devices are contact lenses, more preferably soft hydrogel contact lenses. The transmission wavelengths and percentages described herein may be measured on various thicknesses of lenses using, for instance, the methodologies described in the Examples. By way of example, a preferred center thickness for measuring transmission spectra in a soft contact lens may be from 80 to 100 microns, or from 90 to 100 microns or from 90 to 95 microns. Typically, the measurement may be made at the center of the lens using, for instance, a 4 nm instrument slit width.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

Water concentration %: at least 20%, or at least 25% and up to 80% or up to 70%

Haze: 30% or less, or 10% or less

Advancing dynamic contact angle (Wilhelmy plate method): 100° or less, or 80° or less; or 50° or less Tensile Modulus (psi): 120 or less, or 80 to 120

Oxygen permeability (Dk, barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Compounds of the invention may be used with other products, in addition to ophthalmic devices. For instance, the compounds may be used in windows (e.g., vehicle or building windows), or optical equipment, such as binoculars and cameras, and the like. In such use, the compounds may, for instance, be coated on the surface of the device. To facilitate coating, the compound may be dissolved in a solvent.

The following clauses list non-limiting embodiments of the disclosure:

1. A compound having a visible light absorption maximum between 430 and 480 nm and a full width half maximum (FWHM) at the visible light absorption maximum of at least 35 nm and up to 100 nanometers, wherein the compound is photostable (e.g., when measured according to ICH guideline Q1B).
2. The compound of clause 1 wherein the visible light absorbance maximum is between 440 nm and 470 nm.
3. The compound of any one of clause 1 to 2 wherein the FWHM at the visible light absorption maximum is at least 40 nm and up to 95 nm.
4. The compound of any one of clauses 1 to 3 wherein photostability comprises a loss of absorbance at the visible light absorption maximum of no more than 20 percent.
5. A compound having a visible light absorption maximum between 430 and 480 nm and a full width half maximum (FWHM) at the visible light absorption maximum of at least 35 nm and up to 100 nanometers, wherein the compound is more photostable than macular pigment (e.g., when measured according to ICH guideline Q1B).
6. A compound according to any one of clauses 1 to 5, the compound comprising a chromophore having a substructure of formula I:

(I)

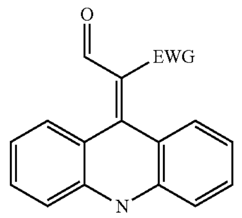

wherein EWG is an electron withdrawing group.

7. The compound of clause 6 wherein EWG is cyano, amide, ester, keto, or aldehyde.
8. The compound of any one of clauses 6 to 7 wherein EWG is cyano.
9. The compound of clause 6 that is of formula II:

(II)

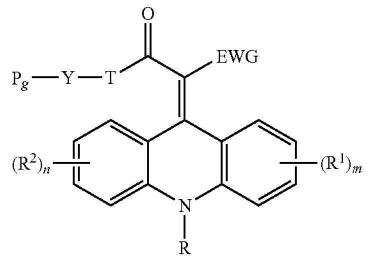

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

10. A compound according to clause 6 that is: (E)-2-(2-cyano-2-(2-methoxy-10-propylacridin-9(10H)-ylidene)acetamido)ethyl methacrylate; or (E)-2-(2-cyano-2-(2-methoxy-10-butylacridin-9(10H)-ylidene) acetamido)ethyl methacrylate.
11. The compound of any one of clauses 1 to 10 wherein photostability comprises a loss of absorbance at the visible light absorption maximum of no more than 20 percent.
12. The compound of any one of clauses 1 to 11, the compound having a molar extinction coefficient of at least 7740.
13. An ophthalmic device comprising a compound according to any one of clauses 1 to 12.
14. A contact lens or intraocular lens that is a polymerization reaction product of a reactive mixture comprising: a monomer suitable for making the ophthalmic device; and (b) a compound according to any one of clauses 1 to 12.

15. A spectacle or sunglass lens comprising (a) a mineral material or an organic material or combination thereof, and (b) a compound according to any one of clauses 1 to 12.

16. The compound, ophthalmic device, or spectacle lens of any one of clauses 1 to 15 that is imported into a country.

17. The compound, ophthalmic device, or spectacle lens of clause 16 wherein the country is the United States of America.

18. A compound having a visible light absorption maximum between 430 and 480 nm and a full width half maximum (FWHM) at the visible light absorption maximum of at least 35 nm and up to 100 nanometers, wherein the compound is photostable (e.g., when measured according to ICH guideline Q1B), and wherein the compound has a molar extinction coefficient of at least 7740 $L \cdot mol^{-1} \cdot cm^{-1}$.

19. The compound of clause 18 wherein the visible light absorbance maximum is between 440 nm and 470 nm.

20. The compound of any one of clauses 18 to 19 wherein the FWHM at the visible light absorption maximum is at least 40 nm and up to 95 nm.

21. The compound of any one of clauses 18 to 20 wherein photostability comprises a loss of absorbance at the visible light absorption maximum of no more than 20 percent.

22. A compound having a visible light absorption maximum between 430 and 480 nm and a full width half maximum (FWHM) at the visible light absorption maximum of at least 35 nm and up to 100 nanometers, wherein the compound is more photostable than macular pigment (e.g., when measured according to ICH guideline Q1B) and wherein the compound has a molar extinction coefficient of at least 7740 $L \cdot mol^{-1} \cdot cm^{-1}$.

23. A compound comprising a chromophore, the chromophore having a substructure of formula I:

(I)

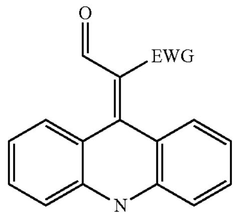

wherein EWG is an electron withdrawing group, the compound having a visible light absorbance maximum in the range of 440 to 480 nm.

24. The compound of clause 23 wherein EWG is cyano, amide, ester, keto, or aldehyde.

25. The compound of any one of clauses 23 to 24 wherein EWG is cyano.

26. The compound of clause 23 that is of formula II:

(II)

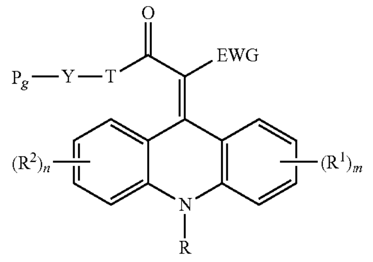

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

27. A compound according to clause 23 that is:
(E)-2-(2-cyano-2-(2-methoxy-10-propylacridin-9(10H)-ylidene)acetamido)ethyl methacrylate; or
(E)-2-(2-cyano-2-(2-methoxy-10-butylacridin-9(10H)-ylidene)acetamido)ethyl methacrylate.

28. The compound of any one of clauses 23 to 27, the compound having a full width half maximum (FWHM) at the visible light absorption maximum of at least 35 nm and up to 100 nanometers, wherein the compound is photostable (e.g., when measured according to ICH guideline Q1B).

29. The compound of clause 28 wherein the visible light absorbance maximum is between 440 nm and 470 nm.

30. The compound of any one of clauses 28 to 29 wherein the FWHM at the visible light absorption maximum is at least 40 nm and up to 95 nm.

31. The compound of any one of clauses 28 to 30 wherein photostability comprises a loss of absorbance at the visible light absorption maximum of no more than 20 percent.

32. The compound of any one of clauses 23 to 31, the compound having a full width half maximum (FWHM) at the visible light absorption maximum of at least 35 nm and up to 100 nanometers, wherein the compound is more photostable than macular pigment (e.g., when measured according to ICH guideline Q1B).

33. The compound of any one of clauses 23 to 32, the compound having a molar extinction coefficient of at least 7740 $L \cdot mol^{-1} \cdot cm^{-1}$.

34. An ophthalmic device comprising a compound according to any one of clauses 18 to 33.

35. A contact lens or intraocular lens that is a polymerization reaction product of a reactive mixture comprising: a monomer suitable for making the ophthalmic device; and (b) a compound according to any one of clauses 18 to 33.

36. A spectacle or sunglass lens comprising (a) a mineral material or an organic material or combination thereof, and (b) a compound according to any one of clauses 18 to 33.

37. A compound having a visible light absorption maximum between 430 and 480 nm and a full width half maximum (FWHM) at the visible light absorption maximum of at least 35 nm and up to 150 nanometers, preferably up to 100 nm, wherein the compound is thermally stable.

38. The compound of clause 37 wherein the compound has a molar extinction coefficient of at least 7740 $L\cdot mol^{-1}\cdot cm^{-1}$.

39. The compound of clause 37 wherein the visible light absorbance maximum is between 440 nm and 470 nm.

40. The compound of any one of clauses 37 to 39 wherein the FWHM at the visible light absorption maximum is at least 40 nm and up to 95 nm.

41. The compound of any one of clauses 37 to 40 wherein thermal stability comprises a loss of absorbance at the visible light absorption maximum of no more than 20 percent.

42. A compound having a visible light absorption maximum between 430 and 480 nm and a full width half maximum (FWHM) at the visible light absorption maximum of at least 35 nm and up to 150 nanometers, preferably up to 100 nanometers, wherein the compound is more thermally stable than macular pigment and wherein the compound optionally has a molar extinction coefficient of at least 7740 $L\cdot mol^{-1}\cdot cm^{-1}$.

43. A compound comprising a chromophore, the chromophore having a substructure of formula I:

(I)

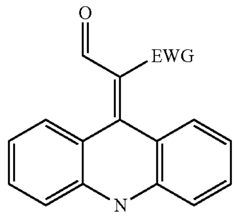

wherein EWG is an electron withdrawing group, the compound having a visible light absorbance maximum in the range of 440 to 480 nm.

44. The compound of clause 43 wherein EWG is cyano, amide, ester, keto, or aldehyde.

45. The compound of any one of clauses 43 to 44 wherein EWG is cyano.

46. The compound of clause 43 that is of formula II:

(II)

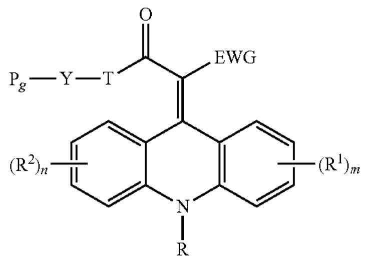

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

47. A compound according to clause 43 that is:
(E)-2-(2-cyano-2-(2-methoxy-10-propylacridin-9(10H)-ylidene)acetamido)ethyl methacrylate; or
(E)-2-(2-cyano-2-(2-methoxy-10-butylacridin-9(10H)-ylidene)acetamido)ethyl methacrylate.

48. The compound of any one of clauses 43 to 47, the compound having a full width half maximum (FWHM) at the visible light absorption maximum of at least 35 nm and up to 150 nanometers, preferably up to 100 nanometers, wherein the compound is thermally stable.

49. The compound of clause 48 wherein the visible light absorbance maximum is between 440 nm and 470 nm.

50. The compound of any one of clauses 48 to 49 wherein the FWHM at the visible light absorption maximum is at least 40 nm and up to 95 nm.

51. The compound of any one of clauses 48 to 50 wherein thermal stability comprises a loss of absorbance at the visible light absorption maximum of no more than 20 percent.

52. The compound of any one of clauses 43 to 51, the compound having a full width half maximum (FWHM) at the visible light absorption maximum of at least 35 nm and up to 150 nanometers, preferably up to 100 nanometers, wherein the compound is more thermally stable than macular pigment.

53. The compound of any one of clauses 43 to 52, the compound having a molar extinction coefficient of at least 7740 $L\cdot mol^{-1}\cdot cm^{-1}$.

54. An ophthalmic device comprising a compound according to any one of clauses 37 to 53.

55. A contact lens or intraocular lens that is a polymerization reaction product of a reactive mixture comprising: a monomer suitable for making the ophthalmic device; and (b) a compound according to any one of clauses 37 to 53.

56. A spectacle or sunglass lens comprising (a) a mineral material or an organic material or combination thereof, and (b) a compound according to any one of clauses 37 to 53.

57. A method for making a compound of formula II:

(II)

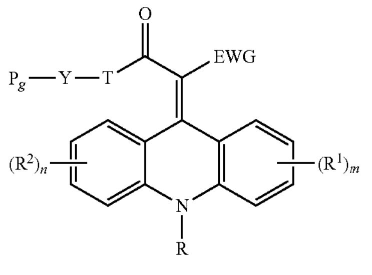

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, benzyl, $SO_3H$, or $SO_3M$ (M is a monovalent cation, such as sodium or potassium), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group, the method comprising:

providing an N-substituted acridone of formula II-A:

(II-A)

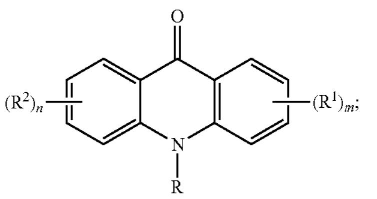

treating the N-substituted acridone with triphenylphosphine dibromide and a reagent of formula:

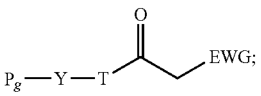

and isolating the compound of formula II.

58. The method of clause 57 wherein EWG is CN.

59. The method of any one of clauses 57 to 58 wherein m and n are 0.

60. The method of any one of clauses 57 to 59 wherein R is $C_1$-$C_6$ alkyl.

61. The method of any one of clauses 57 to 60 wherein T is $NR^6$.

62. The method of clause 57 wherein the compound of formula II is:

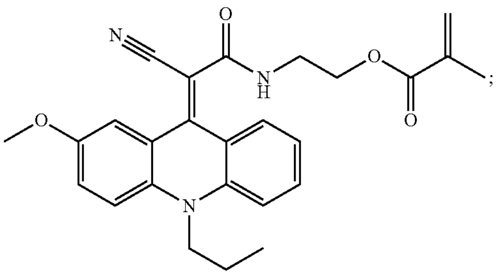

; or

-continued

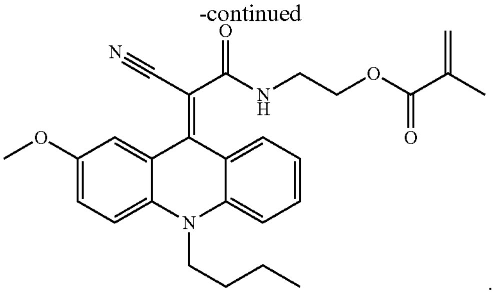

.

Some embodiments of the invention will now be described in detail in the following Examples.

EXAMPLES

Test Methods

Ultraviolet-visible spectra of compounds in solution were measured on a Perkin Elmer Lambda 45, an Agilent Cary 6000i, or an Ocean Optics QE65 PRO (DH-2000-BAL Light Source) UV-VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected. For the Cary instrument, the scan range was 200-800 nm; the scan speed was 600 nm/min; the slit width was 2 nm; the mode was transmission or absorbance; and baseline correction was selected. For the Ocean Optics instrument, the scan range was 200-800 nm; the slit width was 10 μm; the mode was transmission or absorbance; and baseline correction was selected. A baseline correction was performed before samples were analyzed using the autozero function.

Ultraviolet-visible spectra of contact lenses formed in part from the claimed compositions were measured on a Perkin Elmer Lambda 45 UV/VIS, an Agilent Cary 6000i, or an Ocean Optics UV-VIS scanning spectrometer using packing solution. The instrument was thermally equilibrated for at least thirty minutes prior to use. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

Water content was measured gravimetrically. Lenses were equilibrated in packing solution for 24 hours. Each of three test lenses are removed from packing solution using a sponge tipped swab and placed on blotting wipes which have been dampened with packing solution. Both sides of the lens are contacted with the wipe. Using tweezers, the test lens is placed in a tared weighing pan and weighed. Two more samples are prepared and weighed. All weight measurements were done in triplicate, and the average of those values used in the calculations. The wet weight is defined as the combined weight of the pan and wet lenses minus the weight of the weighing pan alone.

The dry weight was measured by placing the sample pans in a vacuum oven which has been preheated to 60° C. for 30 minutes. Vacuum was applied until the pressure reaches at least 1 inch of Hg; lower pressures are allowed. The vacuum valve and pump are turned off, and the lenses are dried for at least 12 hours, typically overnight. The purge valve is opened allowing dry air or dry nitrogen gas to enter. The oven is allowed reach atmospheric pressure. The pans are removed and weighed. The dry weight is defined as the combined weight of the pan and dry lenses minus the weight of the weighing pan alone. The water content of the test lens was calculated as follows: % water content=(wet weight−dry weight)/wet weight×100. The average and standard deviation of the water content were calculated and the average value reported as the percent water content of the test lens.

The mechanical properties of the contact lenses were measured by using a tensile testing machine such as an Instron model 1122 or 5542 equipped with a load cell and pneumatic grip controls. Minus one diopter lens is the preferred lens geometry because of its central uniform thickness profile. A dog-bone shaped sample cut from a minus one diopter spherical lens having a 0.522 inch length, 0.276 inch "ear" width and 0.213 inch "neck" width was loaded into the grips and elongated at a constant rate of strain of 2 inches per minute until it breaks. The center thickness of the dog-bone sample was measured using an electronic thickness gauge prior to testing. The initial gauge length of the sample ($L_o$) and sample length at break ($L_f$) were measured. At least five specimens of each composition were measured, and the average values were used to calculate the percent elongation to break: percent elongation=$[(L_f-L_o)/L_o]\times100$. The tensile modulus was calculated as the slope of the initial linear portion of the stress-strain curve; the units of modulus are pounds per square inch or psi. The tensile strength was calculated from the peak load and the original cross-sectional area: tensile strength=peak load divided by the original cross-sectional area; the units of tensile strength are psi. Toughness was calculated from the energy to break and the original volume of the sample: toughness=energy to break divided by the original sample volume; the units of toughness are in $lbs/in^3$.

A calibrated dual interferometric method was used for measuring contact lens parameters in packing solution. These parameters included equivalent sphere power at multiple apertures (diopters or D), cylinder power at multiple apertures (diopters or D), diameter (millimeters or mm), center thickness (millimeters or mm), sagittal height (millimeters or mm), and root mean squared (RMS) optical path wavefront deviation from lens design target in micrometers or microns (μm) with sphere/cylinder power and coma removed as measured using a 6.5 millimeter aperture. The instrument consists of a custom, propitiatory interferometer for the measurement of wavefront parameters and a Lumetrics OptiGauge® II low-coherence interferometer for the measurement of the dimensional parameters of sagittal height and center thickness. The two individual instruments combined are similar to Lumetrics Clearwave™ Plus, and the software is similar to Lumetrics OptiGauge Control Center v7.0 or higher. With the Clearwave™ Plus, a camera is used to find the lens edge, and then the lens center is calculated, which is then used to align a 1310 nanometer interferometer probe at the lens center for the measurement of sagittal height and center thickness. The transmitted wavefront is also collected in series using a wavefront sensor (shack-Hartmann sensor). Multiple parameters from the transmitted wavefront of the contact lens are measured, and others are calculated from those measurements.

From the data collected, difference terms are calculated by comparing the measured values from the target. These include root mean squared optical path wave front deviation from lens design target in μm (sphere/cylinder power and coma deviation removed) as measured using a 6.5 millimeter aperture (RMS 65), the second equivalent sphere power deviation from lens design target in diopters (D) as measured using a 5 millimeter aperture (PW2EQD), deviation from lens design target diameter in mm (DMD), deviation from lens design target base curve radius as calculated from the measured sagittal height and target lens diameter according to ISO 18369-3 in mm (BCD), and deviation from lens design target center thickness in mm (CTD).

The following abbreviations will be used throughout the Examples and Figures and have the following meanings:

L: liter(s)
mL: milliliter(s)
Equiv. or eq.: equivalent
kg: kilogram(s)
g: gram(s)
mg: milligram(s)
mol: mole(s)
mmol: millimole(s)
M: molar
Da: dalton or g/mole
kDa: kilodalton or an atomic mass unit equal to 1,000 daltons
min: minute(s)
mm: millimeter(s)
cm: centimeter(s)
micrometer(s)
nm: nanometer(s)
λ: wavelength
wt. %: weight percent
Cmpd: compound
TLC: thin layer chromatography
$^1$H NMR: proton nuclear magnetic resonance spectroscopy
UV-VIS: ultraviolet-visible spectroscopy
AU: absorbance units
BC: base curve plastic mold
FC: front curve plastic mold
PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
DMA: N,N-dimethylacrylamide (Jarchem)
HEMA: 2-hydroxyethyl methacrylate (Bimax)
PVP K90: poly(N-vinylpyrrolidone) (ISP Ashland)
TEGDMA: tetraethylene glycol dimethacrylate (Esstech)
Omnirad 1870: blend of bis(2,6-dimethoxybenzoyl)-2,4,4-trimethyl-pentylphosphineoxide and 1-hydroxy-cyclohexyl-phenyl-ketone (IGM Resins or BASF or Ciba Specialty Chemicals) mPDMS: mono-n-butyl terminated monomethacryloxypropyl terminated polydimethylsiloxane ($M_n$=800-1500 daltons) (Gelest)
SiMAA: 2-propenoic acid, 2-methyl-2-hydroxy-3-[3-[1,3,3,3-tetramethyl-1-[(trimethylsilyl)oxy]disiloxanyl]

propoxy]propyl ester (Toray) or 3-(3-(1,1,1,3,5,5,5-heptamethyltrisiloxan-3-yl)propoxy)-2-hydroxypropyl methacrylate Norbloc: 2-(2'-hydroxy-5-methacrylyloxyethylphenyl)-2H-benzotriazole (Janssen)

LED: light emitting diode

D3O: 3,7-dimethyl-3-octanol (Vigon)

DIW: deionized water

IPA: isopropyl alcohol $CDCl_3$: deutrochloroform

HCl: hydrochloric acid

Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.

Example 1—Synthesis of (E)-2-(2-cyano-2-(2-methoxy-10-propylacridin-9(10H)-ylidene)acetamido)ethyl methacrylate (Compound A) as Shown in Scheme 1

Scheme 1

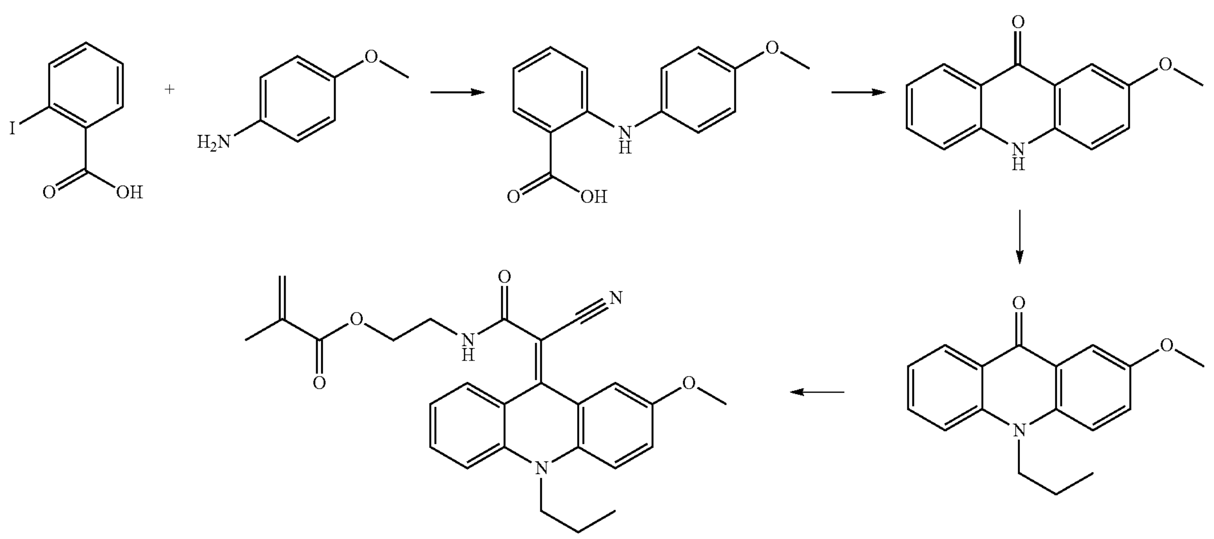

Compound A 2-iodobenzoic acid (12.40 g, 0.05 mol), 12.32 g of 4-methoxyaniline (~2 eq.), 6.91 g of anhydrous potassium carbonate (~0.05 mol), and 300 mg of copper powder (4.76 mmol) were charged in a 100 mL, 3 neck round bottom flask equipped with a magnetic stir bar and reflux condenser. Deionized water (30 mL) was added to the mixture of solids, and the system heated at reflux for 6 hours with constant stirring. The mixture solidified upon cooling to room temperature. The system was diluted with deionized water and gradually poured into 1 normal aqueous hydrochloric acid with stirring. The mixture was stirred at room temperature for 30 minutes, after which it was filtered over a fritted glass funnel and dried in a vacuum oven at 60° C. The residue 2-((4-methoxyphenyl)amino)benzoic acid was washed with 3×100 mL of deionized water and used "as is" for the intramolecular cyclization. $^1H$ NMR ($CDCl_3$)–δ 3.81 (3H, s), 6.66 (1H, t), 6.89-6.93 (3H, m), 7.16 (2H, d), 7.27 (1H, t), 7.99 (1H, d), 9.12 (1H, bs) A 250 mL round bottom flask equipped with a magnetic stir bar and reflux condenser was charged with 12.5 g of 2-((4-methoxyphenyl)amino)benzoic acid and 100 mL of Eaton's acid (10 weight % $P_2O_5$ in methanesulfonic acid). The mixture was heated with constant stirring at 90° C. (mantle temperature) for 5 hours, while monitoring the progress by TLC. Upon cooling to room temperature, the reaction mixture was poured over ice, stirred for 30 minutes, and filtered over a fritted glass funnel. The residue 2-methoxyacridin-9(10H)-one was washed with 3×100 mL of deionized water, followed by acetonitrile, and dried in a vacuum oven at 60° C. $^1H$ NMR (DMSO d6)–δ 3.86 (3H, s), 7.23 (1H, t), 7.41 (1H, dd), 7.52 (1H, d), 7.53 (1H, d), 7.63 (1H, d), 7.70 (1H, dt), 8.23 (1H, d)

A 250 mL round bottom flask equipped with a magnetic stir bar and reflux condenser was charged with 5.4 g of 2-methoxyacridin-9(10H)-one (0.0244 mole) and 12.9 g of cesium carbonate (~1.5 eq.). The solids were dried under vacuum at 80° C., after which the system was placed under a nitrogen blanket and 80 mL of anhydrous N,N-dimethylformamide was added to the flask. 1-bromopropane (6.0 g, ~2 eq.) was added to the flask, and the mixture was heated at 50° C. (mantle temperature) for 36 hours. TLC indicated the presence of two compounds (O-alkylation and N-alkylation). The organics were poured into 200 mL of deionized water and extracted into ~150 mL of ethyl acetate. The organics were then washed with 3×100 mL of water, followed by 3×100 mL of dilute aqueous HCl to remove the O-alkylated acridine byproduct, and a final deionized water wash. TLC of the organics indicated a single compound present at this point, namely 2-methoxy-10-propylacridin-9(10H)-one, which was dried under reduced pressure and used for the subsequent transformation. $^1H$ NMR ($CDCl_3$)–δ1.12 (3H, t), 1.93 (2H, m), 4.28 (2H, dd), 7.25 (1H, ddd), 7.35 (1H, dd), 7.45 (1H, dd), 7.66 (1H, m), 7.96 (1H, d), 7.57 (1H, dd).

A 250 mL, three neck round bottom flask equipped with a magnetic stir bar and reflux condenser was charged with 4.5 g of 2-methoxy-10-propylacridin-9(10H)-one (0.017 mole) and 6.4 g of N-2-methacryloxyethyl-2-cyanoacetamide (0.033 mole). The system was placed under a nitrogen blanket, and 20 mL of dichloromethane was added to the mixture and stirred until homogeneous. After cooling the system in an ice bath, titanium tetrachloride (4.5 mL, 7.78 g, 0.041 mole) was added to the mixture in a dropwise fashion and stirring continued for an additional 15 minutes. Pyridine 5 mL (4.9 g, 0.06 mole) was added to the mixture, which was allowed to warm up to ambient temperature and then heated to reflux for 8 hours. After cooling the mixture to room temperature, it was poured over dilute aqueous HCl, and the product mixture was extracted into dichloromethane. Volatiles were evaporated under reduced pressure, and the product Compound A was purified by flash chromatography. $^1$H NMR ($CDCl_3$)–δ1.07 (3H, t), 1.87 (3H, s), 1.91 (2H, m), 3.58 (2H, dd), 3.85 (3H, s), 4.07 (2H, dd), 4.18 (2H, t), 5.5 (1H, dd), 6.03 (1H, ss), 6.07 (1H, t), 7.07 (1H, t), 7.14 (1H, dd), 7.23 (2H, two doublets), 7.48 (1H, m), 7.92 (1H, bs).

Example 2—Synthesis of (E)-2-(2-cyano-2-(2-methoxy-10-butylacridin-9(10H)-ylidene)acetamido) ethyl methacrylate (Compound B) as Shown in Scheme 2

Scheme 2

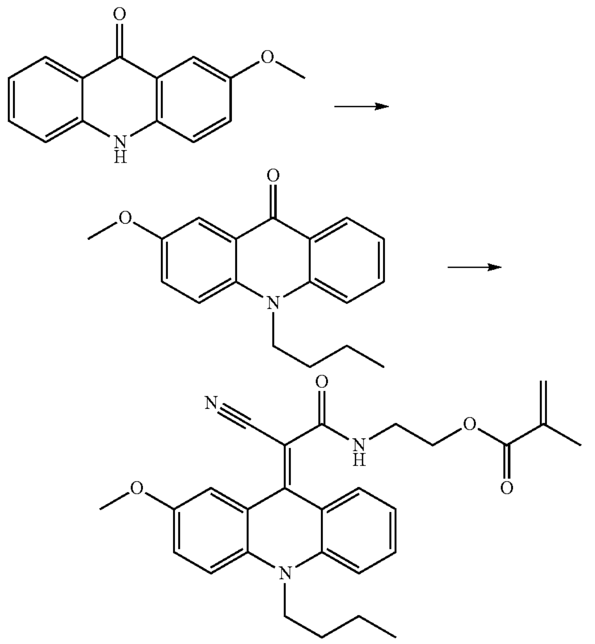

Compound B

A 200 mL round bottom flask equipped with a magnetic stir bar and reflux condenser was charged with 10.0 g of 2-methoxyacridin-9(10H)-one (0.044 mole) and 19.6 g of cesium carbonate (~1.25 eq.). The solids were dried under vacuum at 80° C., after which the system was placed under a nitrogen blanket, and 60 mL of anhydrous DMSO was added to the flask. 1-bromobutane (7.55 g, 1.25 eq.) was added to the flask, and the mixture was heated at 110° C. (mantle temperature) for 6 hours. Two products, very close in retention factor and inseparable by chromatography, were observed by TLC. The cooled suspension was poured over 500 mL of deionized water, and the mixture was stirred for 30 minutes at room temperature. The organics were extracted into ethyl acetate and washed with 3×200 mL of deionized water. NMR of the organics indicated the presence of the 0-alkylated acridine derivative in addition to the desired compound, 2-methoxy-10-butylacridin-9(10H)-one. This material can be used "as is" for the Knoevenagel condensation. Preferably, the crude product was washed with dilute aqueous HCl to remove the O-alkylated acridine derivative, resulting in pure 2-methoxy-10-butylacridin-9 (10H)-one. $^1$H NMR ($CDCl_3$)–δ1.05 (3H, t), 1.55 (2H, m), 1.82 (2H, m), 4.31 (2H, dd), 7.25 (1H, ddd), 7.34 (1H, dd), 7.45 (1H, dd), 7.68 (1H, m), 7.96 (1H, d), 8.56 (1H, dd).

A 250 mL, three neck round bottom flask equipped with a magnetic stir bar and reflux condenser was charged with 10.0 of the crude product mixture containing 2-methoxy-10-butylacridin-9(10H)-one and 15 g of N-2-methacryloxy-ethyl-2-cyanoacetamide. The system was placed under a nitrogen blanket, 150 mL of dichloromethane was added to the mixture and stirred until homogeneous. After cooling the system in an ice bath, titanium tetrachloride (10 mL, 17.3 g, 1.092 mole) was added to the mixture in a dropwise fashion and stirring continued for an additional 15 minutes. Pyridine 10 mL (9.82 g, 0.12 mole) was added to the mixture, which was allowed to warm up to ambient temperature and then heated to reflux for 8 hours. TLC indicated the presence of several compounds including the unreacted O-alkylated derivative present in the starting material mixture. The major product, Compound B, was a slightly more polar, dark brownish orange species, which was isolated after quenching the system in dilute aqueous HCl, followed by aqueous extractions, and chromatography. $^1$H NMR ($CDCl_3$)–δ1.04 (3H, t), 1.51 (2H, m), 1.87 (3H, s, 2H, m), 3.58 (2H, dd), 3.84 (3H, s), 4.12 (2H, dd), 4.19 (2H, t), 5.55 (1H, dd), 6.03 (1H, bs), 6.07 (1H, t), 7.07 (1H, t), 7.15 (1H, dd), 7.25 (2H, two doublets), 7.48 (1H, t), 7.75 (1H, bs), 7.92 (1H, bs).

An Alternative Synthesis of Compound B is Shown in Scheme 3

Scheme 3

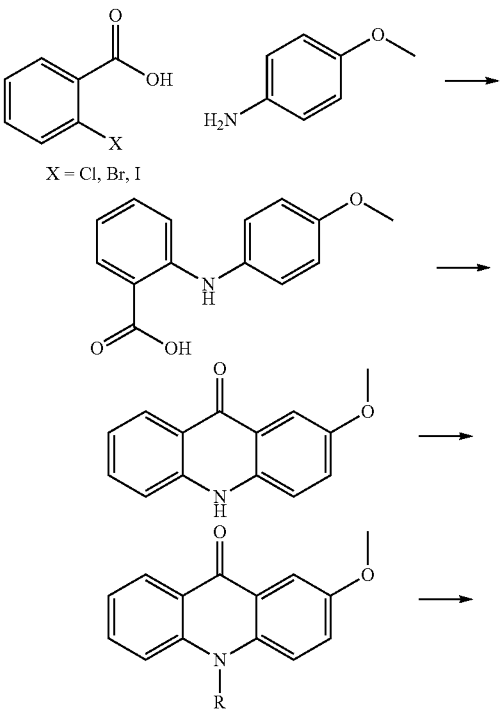

-continued

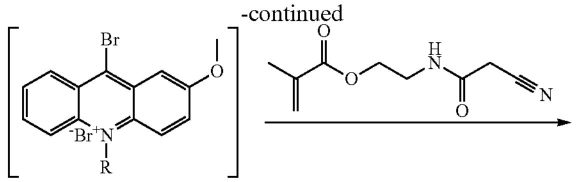

Not Isolated

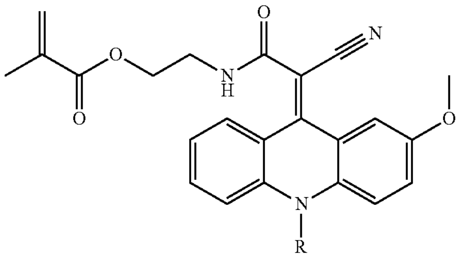

Compound B
R = n-butyl

Synthesis of (E)-2-(2-(10-butyl-2-methoxyacridin-9(10H)-ylidene)-2-cyanoacetamido)ethyl methacrylate or Compound B when R is n-butyl: A 3 neck 500 mL RBF equipped with a magnetic stir bar and a reflux condenser was charged with 9.43 g of triphenylphosphine (36 mmol) and 120 mL of anhydrous dichloromethane. Bromine (5.76 g, 33 mmol) was added dropwise to the solution, which was stirred at room temperature for an additional 30 minutes, after which, 10-butyl-2-methoxyacridin-9(10H)-one (8.43 g, 30 mmol) was added to the mixture and heated to reflux for 18 hours. 2-(2-cyanoacetamido)ethyl methacrylate (8.23 g, 36 mmol, 1.4 eq.) was added to the reaction mixture which was heated and stirred for an additional 8 hours. Very little starting material was observed at this point by TLC and an orange-brown compound was observed at the baseline. The mixture was cooled to room temperature, 150 mL of aqueous sodium carbonate (~10.6 g, 100 mmol dissolved $Na_2CO_3$) was added and the mixture stirred for 30 minutes. Treatment with base resulted in the desired compound. The aqueous layer was extracted with additional dichloromethane. The organics were removed under reduced pressure, and the product purified by chromatography. The crude material was first flushed through silica gel using dichloromethane and ethyl acetate to remove the polar components. Then, a second pass using ethyl acetate/hexanes or diethyl ether/hexanes after loading the material with a minimal amount of methylene chloride provided the desired product in yields >80%.

Select absorbance properties of Compounds A and B are shown in Table 1.

TABLE 1

| | $\lambda_{max}$ | | | | Extinction | |
|---|---|---|---|---|---|---|
| Cmpd | wavelength (nm) | Abs | Pathlength (cm) | Concentration (M) | Coefficient ($M^{-1}cm^{-1}$) | FWHM[1] (nm) |
| A | 463 | 1.312186 | 1 | 0.0001 | 13121.86 | 64 |
| B | 464 | 1.261670 | 1 | 0.0001 | 12616.70 | 62 |

[1]Full width half maximum (FWHM) at $\lambda_{max}$

The UV-VIS absorbance spectra of 0.1 mM methanolic solutions of Compound A and Compound B are shown in FIG. 1 and are superimposed on the literature spectrum of macular pigment.

Example 3—Contact Lenses

A reactive monomer mixture was prepared composed of 77 weight percent of the formulation listed in Table 2, and 23 weight percent of the diluent D3O. The reactive monomer mixture was filtered through a 3 μm filter using a stainless-steel syringe under pressure.

TABLE 2

| Component (weight %) | Ex. 3A | Ex. 3B |
|---|---|---|
| mPDMS | 30.9 | 30.9 |
| SiMAA | 27.9 | 27.9 |
| DMA | 23.92 | 23.92 |
| HEMA | 5.94 | 5.94 |
| TEGDMA | 1.5 | 1.5 |
| PVP K90 | 7 | 7 |
| Omnirad 1870 | 0.34 | 0.34 |
| Norbloc | 2 | 2 |
| Compound A | 0.5 | 0 |
| Compound B | 0 | 0.5 |

The reactive monomer mixture was degassed at ambient temperature by applying vacuum (40 torr) for at least 20 minutes. Then, in a glove box with a nitrogen gas atmosphere and less than about 0.1-0.2 percent oxygen gas, about 75 μL of the reactive mixture was dosed using an Eppendorf pipet at room temperature into the FC made of 90:10 (w/w) Z/TT blend. The BC made of 90:10 (w/w) Z:TT blend was then placed onto the FC. The molds were equilibrated for a minimum of twelve hours in the glove box prior to dosing. Pallets each containing eight mold assemblies were transferred into an adjacent glove box maintained at 62° C., and the lenses are cured from the top and the bottom using 405 nm LED lights having an intensity of about 2.0 $mW/cm^2$ for 10 minutes.

The lenses were manually de-molded and released by suspending the lenses in about one liter of 70 percent IPA for about one hour, followed by soaking two more times with fresh 70 percent IPA for 30 minutes; then overnight in DIW; followed by fresh DIW for 30 minutes; and then with packing solution for 30 minutes. Finally, the lenses were equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels.

Figure 2:
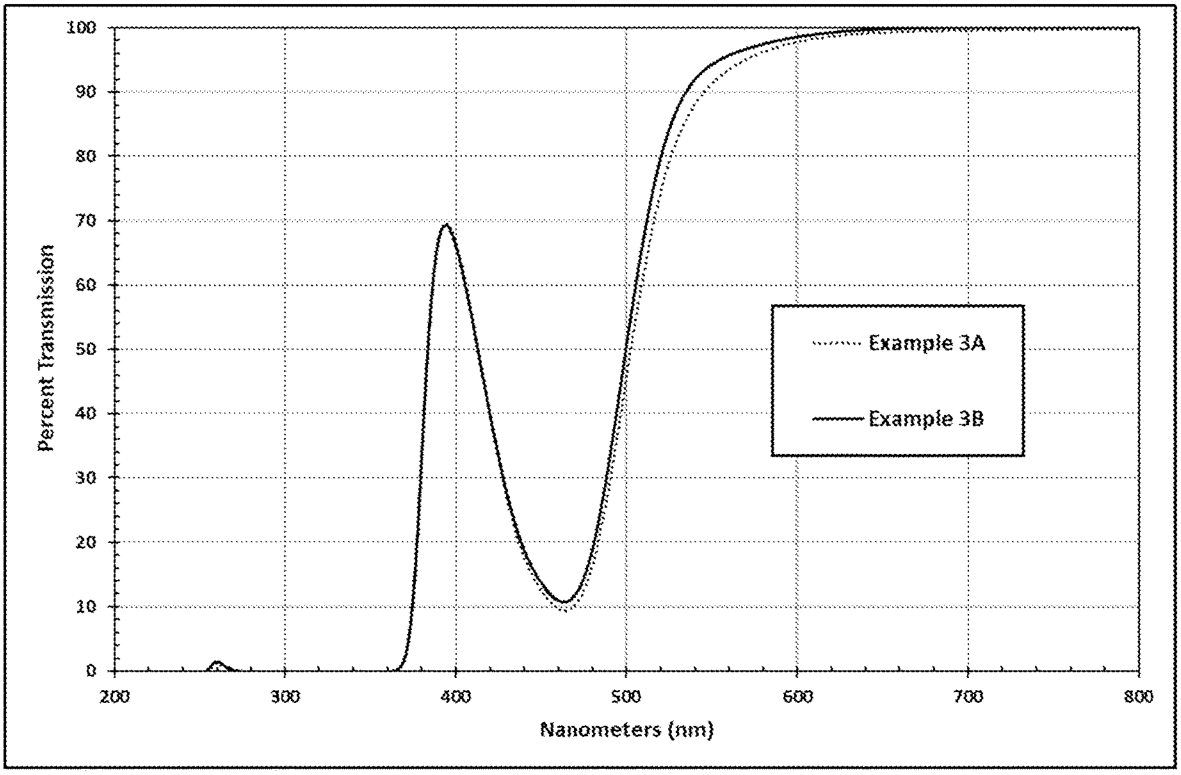
FIG. 2 shows UV-VIS transmission spectra of contact lenses prepared from Compound B.

The UV-VIS transmission spectra of two different sets of lenses (Examples 3A and 3B) in borate buffered packing solution are shown in FIG. 2.

Example 4: Thermal and Photochemical Stability Testing

A reactive monomer mixture was prepared composed of 77 weight percent of the formulation listed in Table 3, and 23 weight percent of the diluent D3O. From that reactive monomer mixture, lenses were fabricated on a pilot manufacturing line using double sided 395 nm LED cure with an intensity of 1.5 $mW/cm^2$ for 4 minutes followed by 5 $mW/cm^2$ for 4 minutes were used to cure the lenses. The lenses were packaged in standard blister packages with borate buffered packing solution containing about 50 ppm methyl ether cellulose; and the lenses (Ex. 4A) were sterilized at 121° C. for about 18 minutes.

TABLE 3

| Component (weight %) | Ex. 4A |
|---|---|
| mPDMS | 31 |
| SiMAA | 28 |
| DMA | 24.01 |
| HEMA | 6 |
| TEGDMA | 1.5 |
| PVP K90 | 7 |
| Omnirad 1870 | 0.34 |
| Norbloc | 2 |
| Visibility Tint | 0.06 |
| Compound B | 0.09 |

Figure 3:
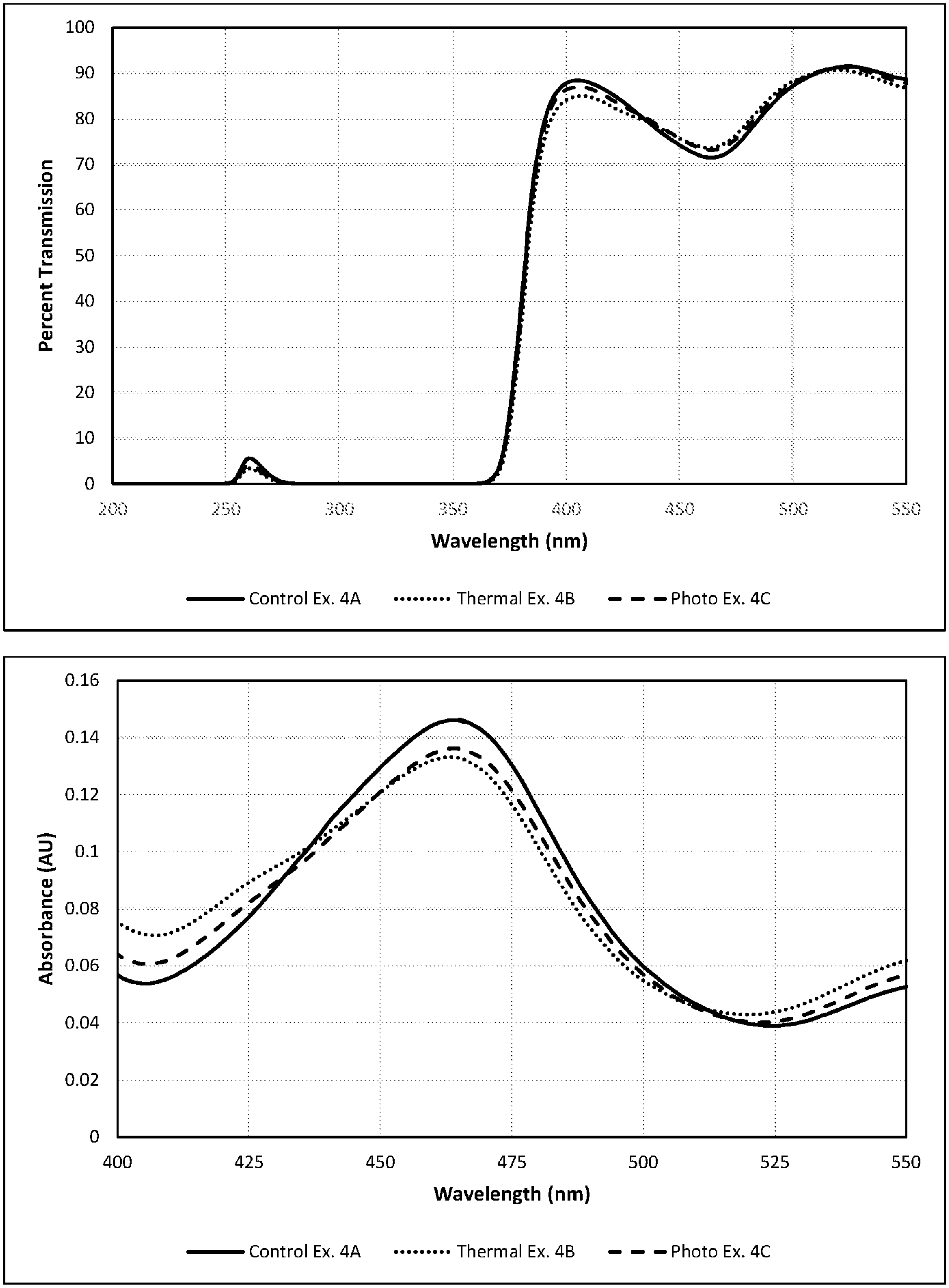
FIG. 3 shows UV-VIS transmission spectra of contact lenses prepared from Compound B before and after either thermal or photo-stress treatments.

Ex. 4A lenses (Control lenses) were removed from their original blister packages and placed into individual glass vials containing 5 mL of borate buffered packing solution. The vials containing these lenses were stored in a stability chamber at 89° C. for one month. The lens parameters, mechanical properties, and UV-VIS spectral properties (average percent transmission across a range of wavelengths) of these thermally treated lenses (Ex. 4B) were subsequently measured and compared to the control lenses. These data are shown in Tables 4-6. Standard deviations are shown in parentheses. The UV-VIS spectra Examples 4A and 4B are shown in FIG. 3.

Blister packages containing Ex. 4A lenses were placed in a controlled photostability chamber (foil side down, bowl side up, so that the lenses in the bowls could be exposed to light). The photostability chambers were maintained at 25° C.±2° C. and ambient relative humidity. These lenses were then exposed sequentially to 1.5 million lux hours of visible light (168.8 hours of exposure) and 259.4 watt-hours/$m^2$ of ultraviolet light (16.2 hours of exposure). The lens parameters, mechanical properties, and UV-VIS spectral properties (average percent transmission across a range of wavelengths) of these photo-stressed lenses (Ex. 4C) were subsequently measured and compared to the control lenses. These data are shown in Tables 4-7. Standard deviations are shown in parentheses. The UV-VIS spectrum of Ex. 4C is also shown in FIG. 3.

TABLE 4

Lens Parameters

| Lens Parameters | Ex. 4A | Ex. 4B | Ex. 4C |
|---|---|---|---|
| Lens Diameter (mm) | 14.44 (0.01) | 14.50 (0.01) | 14.45 (0.01) |
| Base Curve Radius (mm) | 8.61 (0.01) | 8.59 (0.07) | 8.59 (0.01) |
| Center Thickness (mm) | 0.085 (0.002) | 0.086 (0.001) | 0.086 (0.001) |
| PW2EQD (D) | −0.07 | −0.02 | −0.006 |
| RMS_65 (μm) | 0.03 | 0.06 | 0.03 |

TABLE 5

Mechanical Properties

| Mechanical Properties | Ex. 4A | Ex. 4B | Ex. 4C |
|---|---|---|---|
| Modulus (psi) | 99 (5) | 113 (9) | 100 (5) |
| Elongation (%) | 214 (48) | 162 (39) | 231 (57) |
| Tensile strength (psi) | 106 (24) | 96 (20) | 110 (26) |
| Toughness (in-lb/$in^3$) | 113 (41) | 84 (34) | 135 (48) |
| Water (wt. %) | 38.2 (0) | 38.7 (0) | 39.8 (0) |

TABLE 6

Spectral Properties

| | Average Percent Transmission across the Spectral Range | | |
|---|---|---|---|
| Spectral Range | Ex. 4A | Ex. 4B | Ex. 4C |
| Visible (380-780 nm) | 86.8 | 86.4 | 87.0 |
| UVA (315-380 nm) | 2.5 | 2.5 | 2.8 |
| UVB (280-315 nm) | 0.0 | 0.0 | 0.0 |
| 464 nm | 73.08 | 73.6 | 71.43 |
| 400-500 nm | 79.9 | 80.1 | 80.3 |

TABLE 7

Thermal Stability and Photostability at Visible Light Absorbance Maximum

| Ex. 4A (control) Absorbance[1] | Ex. 4B Absorbance | Ex. 4B % Change | Ex. 4C Absorbance | Ex. 4C % Change |
|---|---|---|---|---|
| 0.1461 | 0.1328 | 9.1 | 0.1361 | 6.8 |

[1]at visible light absorbance maximum

As shown by the small changes in the lens parameters, mechanical properties, and UV-VIS transmission spectra after the thermal treatment or light exposure, chromophores having the chemical substructure of Formula I, such as compound B, appear to be both thermally stable and photostable in contact lenses while substantially mimicking the UV-VIS spectrum of macular pigment.

I claim:

1. A contact lens or intraocular lens that is a polymerization reaction product of a reactive mixture comprising: (a) a monomer suitable for making the contact lens or intraocular lens; and (b) a compound having a visible light absorption maximum between 450 and 475 nm and a full width half maximum (FWHM) at the visible light absorption maximum of at least 35 nm and up to 150 nanometers, wherein the compound is photostable, and wherein the compound has a molar extinction coefficient of at least 7740 $L \cdot mol^{-1} \cdot cm^{-1}$.

2. The contact lens or intraocular lens of claim 1 wherein the FWHM at the visible light absorption maximum is at least 40 nm and up to 95 nm.

3. The contact lens or intraocular lens of claim 1 wherein photostability comprises a loss of absorbance at the visible light absorption maximum of no more than 20 percent.

4. The contact lens or intraocular lens of claim 1 wherein the compound is of formula II:

(II)

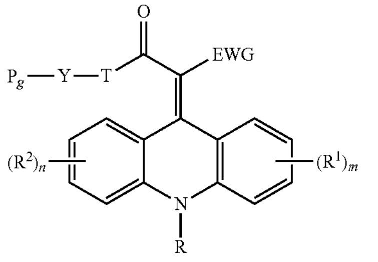

wherein m and n are independently 0, 1, 2, 3, or 4; T is a bond, O, or $NR^6$, wherein $R^6$ is H, $C_1$-$C_6$ alkyl, cycloalkyl, heterocycloalkyl, aryl, heteroaryl, or Y—$P_g$; R is H, $C_1$-$C_6$ alkyl, cycloalkyl, heterocycloalkyl, aryl, or heteroaryl; Y is a linking group; $P_g$ is a polymerizable group; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, benzyl, $SO_3H$, or $SO_3M$ (M is a monovalent cation), wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

5. The contact lens or intraocular lens of claim 1 wherein the compound is of formula III:

(III)

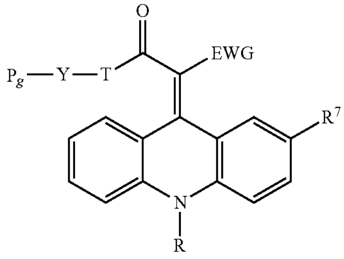

wherein:

T is $NR^6$, wherein $R^6$ is H, or $C_1$-$C_6$ alkyl;

R is $C_1$-$C_6$ alkyl;

Y is a linking group;

$P_g$ is a polymerizable group;

$R^7$ is $C_1$-$C_6$ alkoxy; and

EWG is cyano.

6. The contact lens or intraocular lens of claim 1 wherein the compound is:

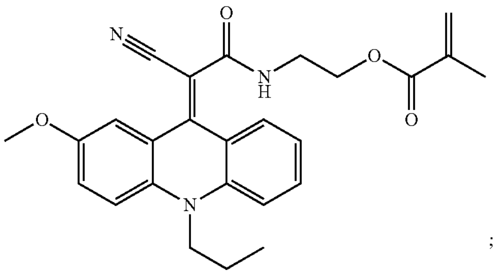

; or

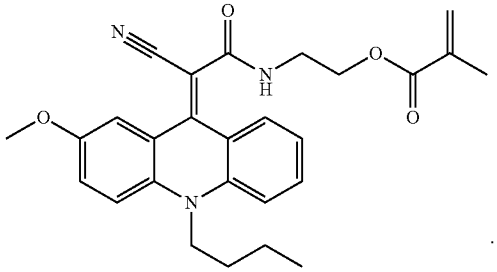

.

* * * * *